(12) United States Patent
Kim et al.

(10) Patent No.: US 9,433,607 B2
(45) Date of Patent: Sep. 6, 2016

(54) **COMPOSITION FOR PREVENTION OR TREATMENT OF CANCER COMPRISING N-METHYLENENAPHTHO[2,1-*B*]FURAN-2-CARBOHYDRAZIDE DERIVATIVES AS AN ACTIVE INGREDIENT**

(71) Applicant: KOREA RESEARCH INSTITUTE OF BIOSCIENCE AND BIOTECHNOLOGY, Daejeon (KR)

(72) Inventors: Bo Yeon Kim, Daejeon (KR); Krisada Sakchaisri, Daejeon (KR); Sun Ok Kim, Daejeon (KR); Ramegowda Thimmegowda Naraganahalli, Daejeon (KR); Nak Kyun Soung, Daejeon (KR); Jong Seog Ahn, Daejeon (KR); Joonsung Hwang, Daejeon (KR); In Ja Ryoo, Daejeon (KR); Jae-Hyuk Jang, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 14/641,065

(22) Filed: Mar. 6, 2015

(65) Prior Publication Data

US 2015/0182502 A1 Jul. 2, 2015

Related U.S. Application Data

(63) Continuation-in-part of application No. PCT/KR2013/008084, filed on Sep. 6, 2013.

(30) Foreign Application Priority Data

Sep. 7, 2012 (KR) .................. 10-2012-0099412
Sep. 6, 2013 (KR) .................. 10-2013-0107289

(51) Int. Cl.
*A61K 31/40* (2006.01)
*A61K 31/405* (2006.01)
*A61K 31/34* (2006.01)
(Continued)

(52) U.S. Cl.
CPC ........... *A61K 31/405* (2013.01); *A61K 31/343* (2013.01); *A61K 31/4045* (2013.01)

(58) Field of Classification Search
CPC ..................... A61K 31/404; A61K 31/343
USPC ........................ 514/414, 415, 468
See application file for complete search history.

(56) References Cited

FOREIGN PATENT DOCUMENTS

KR 10-2006-0019558 3/2006
WO WO2013/076275 * 5/2013

OTHER PUBLICATIONS

Zhang et al., Discovery and SAR of indole-2-carboxylic acid benzylidene-hydrazides as a new series of potent apotosis inducers using a cell-based HTS assay, *Bioorganic & Medicinal Chemistry* 12:3649-3655 (2004).

(Continued)

*Primary Examiner* — Shengjun Wang
(74) *Attorney, Agent, or Firm* — Klarquist Sparkman, LLP

(57) ABSTRACT

The present invention relates to ethyl(2-methyl-3{(E)-[(naphtho[2,1-b]furan-2-ylcarbonyl)hydrazono]methyl}-1H-indole-1-yl)acetate, the novel mitosis inhibitor. The said ethyl(2-methyl-3{(E)-[(naphtho[2,1-b]furan-2-ylcarbonyl)hydrazono]methyl}-1H-indole-1-yl)acetate not only induces apoptosis by inhibiting tubulin polymerization in the course of mitosis but also displays an excellent anticancer effect in the multi-drug resistant cancer cells, so that it can be effectively used for the treatment of cell proliferative disease including various cancers.

8 Claims, 13 Drawing Sheets

(51) Int. Cl.
*A61K 31/343* (2006.01)
*A61K 31/4045* (2006.01)

(56) References Cited

OTHER PUBLICATIONS

Ravindra et al., Synthesis, antimicrobial and antiinflammatory activities of 1,3,4-oxadiazoles linked to naphtho[2,1-*b*]furan, *Indian Journal of Chemistry* 45B:2506-2511 (2006).

Nagaraja et al., Synthesis of novel nitrogen containing naphtho [2,1-*b*]furan derivatives and investigation of their anti microbial activities, *ARKIVOC* (xv):160-168 (2006).

Shashidhar et al., Synthesis and spectroscopic characterization of metal complexes with naphthofuran-2-carbohydrazide Schiff's base, *Journal of Coordination Chemistry* 60(3):243-256 (2007).

Murugan et al., Synthesis and biological activities of N-[(2'-Substituted phenyl)-1', 3'-thiazol-5-one]-naphtho[2,1-b]furan-2-carboxamide derivatives, *Der Pharma Chemica* 3(4):509-516 (2011).

Caboni et al., "True"Antiandrogens-Selective Non-Ligand-Binding Pocket Disruptors of Androgen Receptor—Coactivator Interactions:Novel Tools for Prostate Cancer, *Journal of Medicinal Chemistry* 55:1635-1644 (2012).

* cited by examiner

COMPOSITION FOR PREVENTION OR TREATMENT OF CANCER COMPRISING N-METHYLENENAPHTHO[2,1-*B*]FURAN-2-CARBOHYDRAZIDE DERIVATIVES AS AN ACTIVE INGREDIENT

CROSS REFERENCE TO RELATED APPLICATIONS

This is a Continuation-in-part of International Application No. PCT/KR2013/008084, filed Sep. 6, 2013, which in turn claims the benefit of Korean Patent Application No. 10-2012-0099412, filed Sep. 7, 2012 and Korean Patent Application No. 10-2013-0107289, filed Sep. 6, 2013. The Korean applications are incorporated by reference herein in their entirety.

BACKGROUND OF THE INVENTION

1. Field of the Invention

The present invention relates to a composition for the prevention and treatment of cell proliferative disease including cancer which comprises ethyl(2-methyl-3{(E)-[(naphtho[2,1-b]furan-2-ylcarbonyl)hydrazono]methyl}-1H-indole-1-yl)acetate, the analogs thereof, or the pharmaceutically acceptable salts thereof as an active ingredient. More particularly, the present invention relates to a compound that can induce apoptosis by depolymerizing microtubules and can have an effect on multi-drug resistant cancer cells.

2. Description of the Related Art

Microtubule is a major component of cytoskeleton, which is composed of tubulin heteropolymer comprising α subunit and β subunit. Microtubule is involved in a variety of cellular functions such as intracellular transportation, maintaining polarity, intracellular signal transduction, cell migration, and cell proliferation, etc. In the course of mitosis, spindle fibers are generated and chromosomes are arranged in the center of cell to be separated later to the opposite side ends. When the spindle fiber is not functioning well, cell division is suppressed, resulting in apoptosis. So, microtubule is in the center of cancer research as a major target of an anti-cancer agent.

Drugs targeting microtubule are largely divided into two groups; one is the drugs playing a role in stabilizing microtubule and the other is the drugs playing a role in instabilizing microtubule. Taxane, pacilitaxel (Taxol), and decetaxel are the microtubule stabilizers playing a role in preventing depolymerization of microtubule and rather working on strengthening the polymerization. Most of the microtubule stabilizers are conjugated to taxane binding site or β-tubulin overlapping site. Microtubule destabilizer is exemplified by cholchicine and *vinca* alkaloid, which is binding to cholchicine or *vinca* binding site. The drug that shows pharmaceutical effect at a lower concentration is the drug targeting microtubule itself rather than the drug affecting microtubule polymer. However, both drugs suppress mitosis equally.

The drugs specifically targeting microtubule, that have been used clinically nowadays, are pacilitaxel and *vinca* alkaloid. However, these drugs have a problem of low efficacy because of the acquired resistance and the congenital resistance of cancer cell. Drug resistance is closely related to the expression of the protein involved in multidrug resistance such as P-glycoprotein (P-gp). Resistance can also be induced by the change or mutation of tubulin isotype. Besides, because of the high toxicity (particularly neurotoxicity) of a tubulin inhibitor, researchers hesitate in developing a tubulin inhibitor. Therefore, recent studies have been focused on the development of a novel tubulin inhibitor that has a low neurotoxicity and is not affected by the mechanisms of anticancer drug resistance.

Thus, the present inventors screened the materials capable of inhibiting cell proliferation from small-molecule library in order to identify a therapeutic material effective in treating cell proliferative disease. As a result, the inventors confirmed that ethyl(2-methyl-3-{(E)-[(naphtho[2,1-b]furan-2-ylcarbonyl)hydrazono]methyl}-1H-indole-1-yl)acetate and the analogs thereof could suppress mitosis significantly, so that the compound could be effectively used for the composition for treating cell proliferative disease including cancer, leading to the completion of this invention.

SUMMARY OF THE INVENTION

It is an object of the present invention to provide a pharmaceutical composition for the prevention and treatment of cell proliferative disease comprising ethyl(2-methyl-3{(E)-[(naphtho[2,1-b]furan-2-ylcarbonyl)hydrazono]methyl}-1H-indole-1-yl)acetate, the analogs thereof, or the pharmaceutically acceptable salts thereof as an active ingredient.

To achieve the above object, the present invention provides a pharmaceutical composition for the prevention and treatment of cell proliferative disease comprising ethyl(2-methyl-3{(E)-[(naphtho[2,1-b]furan-2-ylcarbonyl)hydrazono]methyl}-1H-indole-1-yl)acetate, the analogs thereof, or the pharmaceutically acceptable salts thereof as an active ingredient.

The present invention also provides a health food for the prevention and improvement of cell proliferative disease comprising ethyl(2-methyl-3{(E)-[(naphtho[2,1-b]furan-2-ylcarbonyl)hydrazono]methyl}-1H-indole-1-yl)acetate, the analogs thereof, or the pharmaceutically acceptable salts thereof as an active ingredient.

The present invention further provides a method for treating cancer containing the step of administering a pharmaceutically effective dose of ethyl(2-methyl-3{(E)-[(naphtho[2,1-b]furan-2-ylcarbonyl)hydrazono]methyl}-1H-indole-1-yl)acetate, the analogs thereof, or the pharmaceutically acceptable salts thereof to a subject having cell proliferative disease.

The present invention also provides a method for preventing cancer containing the step of administering a pharmaceutically effective dose of ethyl(2-methyl-3{(E)-[(naphtho[2,1-b]furan-2-ylcarbonyl)hydrazono]methyl}-1H-indole-1-yl)acetate, the analogs thereof, or the pharmaceutically acceptable salts thereof to a subject.

The present invention also provides a use of ethyl(2-methyl-3{(E)-[(naphtho[2,1-b]furan-2-ylcarbonyl)hydrazono]methyl}-1H-indole-1-yl)acetate, the analogs thereof, or the pharmaceutically acceptable salts thereof for a pharmaceutical composition for the prevention and treatment of cell proliferative disease.

The present invention also provides a use of ethyl(2-methyl-3{(E)-[(naphtho[2,1-b]furan-2-ylcarbonyl)hydrazono]methyl}-1H-indole-1-yl)acetate, the analogs thereof, or the pharmaceutically acceptable salts thereof for a health food for the prevention and improvement of cell proliferative disease.

Advantageous Effect

The compound or the pharmaceutically acceptable salts thereof of the present invention can induce apoptosis by depolymerizing microtubule and can be effective on even those cancer cells displaying multi-drug resistance. Therefore, the composition comprising the compound, the analogs thereof, or the pharmaceutically acceptable salts thereof of the present invention can be effectively used for the treatment of cell proliferative disease including many types of cancers.

BRIEF DESCRIPTION OF THE DRAWINGS

The application of the preferred embodiments of the present invention is best understood with reference to the accompanying drawings, wherein.

DESCRIPTION OF THE PREFERRED EMBODIMENTS

Figure 1:
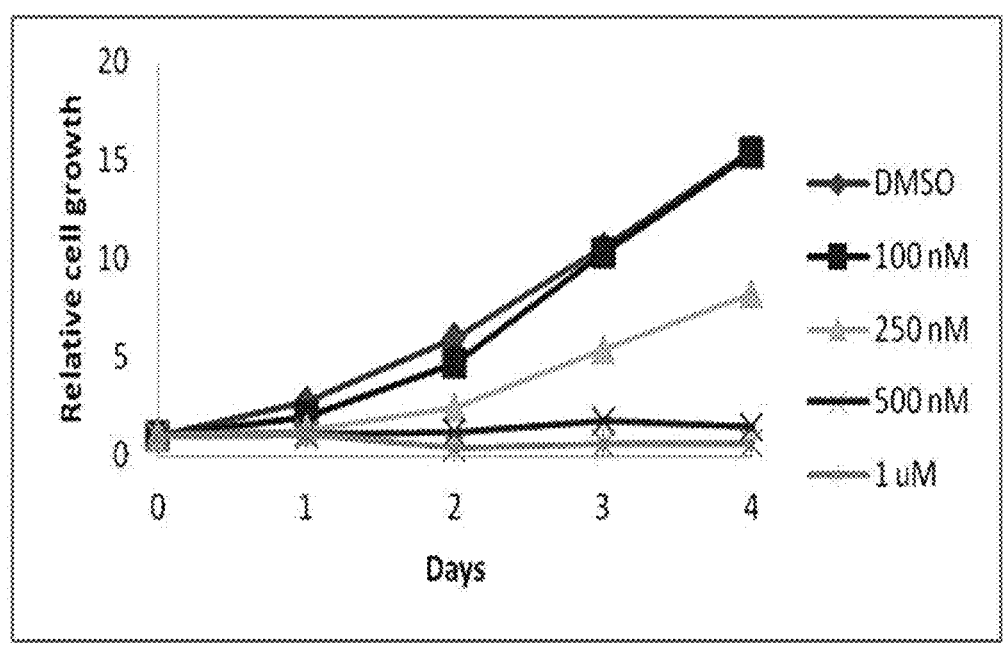
FIG. 1 is a diagram illustrating the anti-proliferative activity of ethyl(2-methyl-3{(E)-[(naphtho[2,1-b]furan-2-ylcarbonyl)hydrazono]methyl}-1H-indole-1-yl)acetate in HeLa cells.

Hereinafter, the present invention is described in detail.

The present invention provides a pharmaceutical composition for the prevention or treatment of cell proliferative disease comprising ethyl(2-methyl-3{(E)-[(naphtho[2,1-b]furan-2-ylcarbonyl)hydrazono]methyl}-1H-indole-1-yl)acetate represented by the below formula 1 or the pharmaceutically acceptable salts thereof as an active ingredient.

[Formula 1]

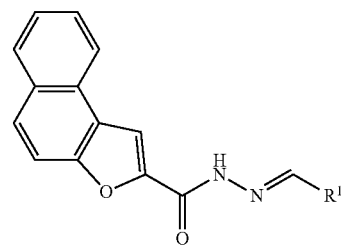

(In the formula 1,
$R^1$ is

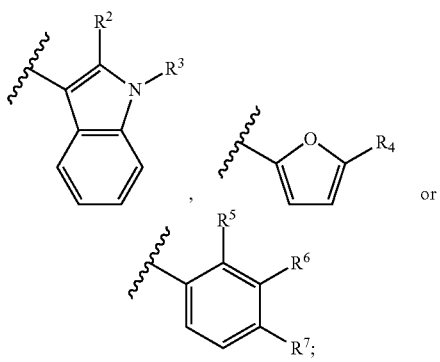

or $R^2$ is hydrogen, or $C_{1-5}$ straight or branched alkyl;
$R^3$ is hydrogen, $C_{1-5}$ straight or branched alkyl,

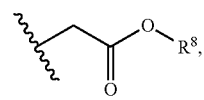

$C_{1-5}$ straight or branched alkenyl, or $C_{1-5}$ straight or branched cyanoalkyl, wherein $R^8$ is $C_{1-5}$ straight or branched alkyl;

R⁴ is nitro, or

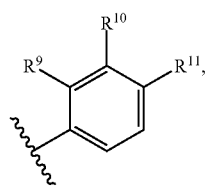

wherein $R^9$, $R^{10}$ and $R^{11}$ are independently hydrogen, halogen, nitro, or $C_{1-5}$ straight or branched alkyl;

$R^5$, $R^6$ and $R^7$ are independently hydrogen, hydroxy, $C_{1-5}$ straight or branched alkoxy, or $C_{1-5}$ straight or branched phenylalkoxy).

The compound represented by the above formula 1 can be selected from the group consisting of the compounds represented by the below formula 2~formula 12, but not always limited thereto:

[Formula 2]

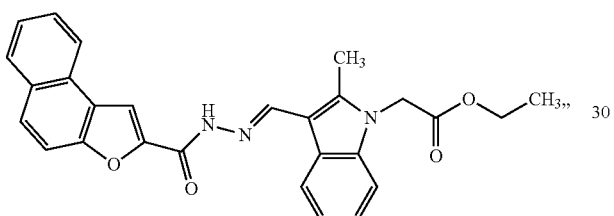

[Formula 3]

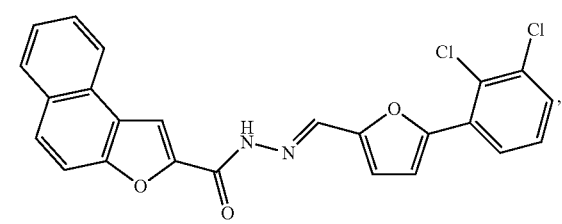

[Formula 4]

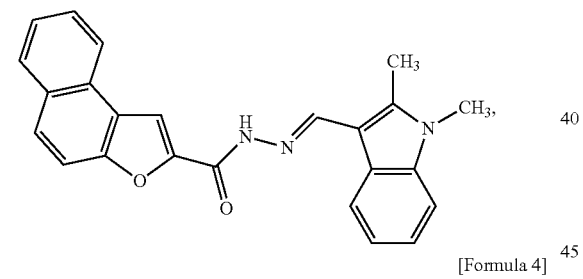

[Formula 5]

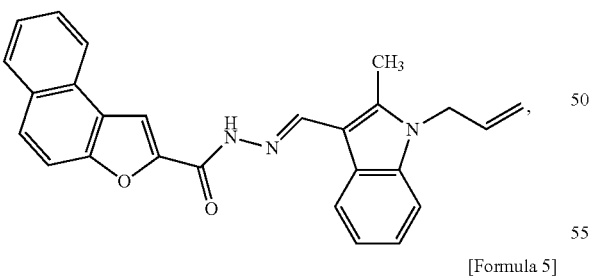

[Formula 6]

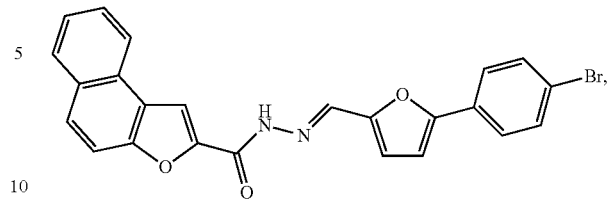

[Formula 7]

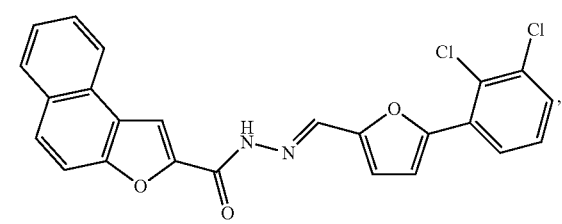

[Formula 8]

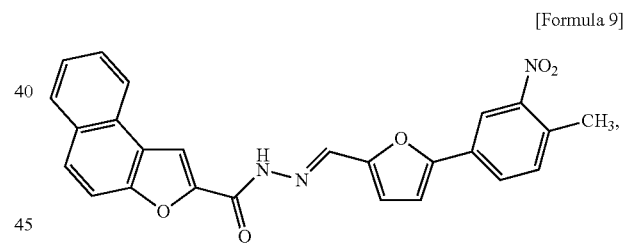

[Formula 9]

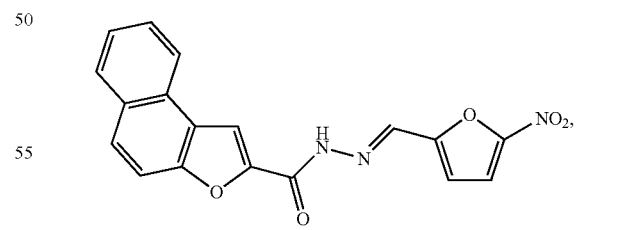

[Formula 10]

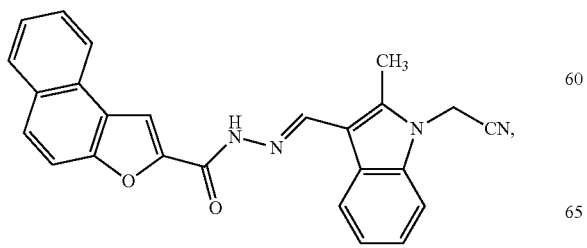

[Formula 11]

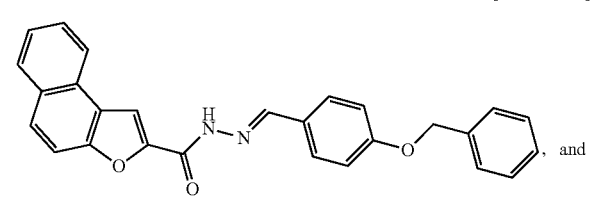

, and

-continued

[Formula 12]

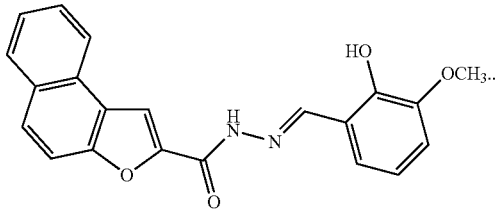

The cell proliferative disease herein can be cancer, but not always limited thereto.

The cancer herein is selected from the group consisting of rectal cancer, prostate cancer, breast cancer, lung cancer, stomach cancer, liver cancer, leukemia, glioma, and uterine cervical cancer, but not always limited thereto.

The ethyl(2-methyl-3{(E)-[(naphtho[2,1-b]furan-2-ylcarbonyl)hydrazono]methyl}-1H-indole-1-yl)acetate represented by formula 1 is supposed to induce the depolymerization of microtubule, but not always limited thereto.

The ethyl(2-methyl-3{(E)-[(naphtho[2,1-b]furan-2-ylcarbonyl)hydrazono]methyl}-1H-indole-1-yl)acetate represented by formula 1 is preferably conjugated to the cholchicine binding site of tubulin, but not always limited thereto.

The ethyl(2-methyl-3{(E)-[(naphtho[2,1-b]furan-2-ylcarbonyl)hydrazono]methyl}-1H-indole-1-yl)acetate represented by formula 1 is preferably subject to induce apoptosis by arresting cell cycle in G2 or M phase, but not always limited thereto.

The ethyl(2-methyl-3{(E)-[(naphtho[2,1-b]furan-2-ylcarbonyl)hydrazono]methyl}-1H-indole-1-yl)acetate represented by formula 1 is preferably working on those cancer cells displaying multi-drug resistance, but not always limited thereto.

In a preferred embodiment of the present invention, the present inventors treated HeLa cells with different concentrations of the said compound and then performed MTT assay in order to confirm the anti-proliferative activity of ethyl(2-methyl-3{(E)-[(naphtho[2,1-b]furan-2-ylcarbonyl)hydrazono]methyl}-1H-indole-1-yl)acetate. As a result, the compound was confirmed to inhibit HeLa cell growth dose-dependently (see FIG. 1).

To investigate the anti-proliferative activity of ethyl(2-methyl-3{(E)-[(naphtho[2,1-b]furan-2-ylcarbonyl)hydrazono]methyl}-1H-indole-1-yl)acetate, the compound was treated to each cancer cell line (rectal cancer, prostate cancer, breast cancer, lung cancer, stomach cancer, liver cancer, leukemia, brain cancer, and glioma cell lines) at different concentrations, followed by MTT assay. As a result, the compound was confirmed to inhibit the cell growth in the cell lines of rectal cancer, prostate cancer, breast cancer, lung cancer, stomach cancer, liver cancer, leukemia, brain cancer, and glioma (see Table 2).

To investigate the anti-proliferative activity of ethyl(2-methyl-3{(E)-[(naphtho[2,1-b]furan-2-ylcarbonyl)hydrazono]methyl}-1H-indole-1-yl)acetate further in those cancer cells displaying multi-drug resistance, the compound, doxorubicin, and taxol were treated to K562, MCF7, and so were the multi-drug resistant cell lines thereof, K562/ADR and MCF7/ADR, followed by MTT assay. As a result, the resistant factor in the cell line displaying multi-drug resistance treated with the compound above was 0.2~0.6. The resistant factor, however, was 377~1584 times higher in those multi-drug resistant cell lines treated with doxorubicin and taxol. Therefore, it was confirmed that the above compound had a significant cytotoxic effect in the cancer cell line displaying multi-drug resistance (see Table 3).

To investigate the effect of ethyl(2-methyl-3{(E)-[(naphtho[2,1-b]furan-2-ylcarbonyl)hydrazono]methyl}-1H-indole-1-yl)acetate on cell cycle, the compound was treated to HeLa cells for 17 hours and then cell cycle distribution and mitosis index were investigated. As a result, the compound was confirmed to arrest cell cycle in G2/M phase (see FIG. 2).

To investigate the effect of ethyl(2-methyl-3{(E)-[(naphtho[2,1-b]furan-2-ylcarbonyl)hydrazono]methyl}-1H-indole-1-yl)acetate on the proteins regulating cell division, the tubulin depolymerizing agent nocodazol was treated to HeLa cells and then the proteins involved in the regulation of cell division such as Cdc25C, Cyclin B1, and Plk1 (Polo-like kinase 1) were examined. As a result, in the HeLa cells treated with the compound, Cdc25C was phosphorylated and Cyclin B1 and Plk1 were accumulated in the cell likewise in the cell treated with nocodazol (see FIG. 4).

To investigate whether ethyl(2-methyl-3{(E)-[(naphtho[2,1-b]furan-2-ylcarbonyl)hydrazono]methyl}-1H-indole-1-yl)acetate could induce apoptosis, HeLa cells were treated with DMSO and the said compound for 24 hours or 48 hours, followed by immunoblotting to measure the expressions of apoptosis related proteins such as caspase 3 and PARP. As a result, apoptosis was induced in HeLa cells treated with the compound of the present invention (see FIG. 5).

To confirm the effect of ethyl(2-methyl-3{(E)-[(naphtho[2,1-b]furan-2-ylcarbonyl)hydrazono]methyl}-1H-indole-1-yl)acetate on tubulin polymerization, 5 M of the compound was treated to the cells in the buffer comprising the purified tubulin and GTP. The control group was treated with DMSO and the equal amount of Taxol and vinblastine. Then, each cell group was compared. As a result, the degree of turbidity was lower in the cells treated with tubulin than that in the cells treated with Taxol (see FIG. 6).

To investigate the effect of ethyl(2-methyl-3{(E)-[(naphtho[2,1-b]furan-2-ylcarbonyl)hydrazono]methyl}-1H-indole-1-yl)acetate on intracellular microtubules, HeLa cells were treated with DMSO, Taxol (100 μM), nocodazole (200 mg/ml), and the compound of the present invention respectively for 17 hours. After fixing the cells, immunostaining was performed with Alexa Fluor 488-conjugated anti-tubulin antibody and Hoechst 33342 to investigate α-tubulin and chromosomes. As a result, tubulin polymerization was strengthened in the cells treated with Taxol to display multi-polar spindle fibers with concentrated chromosomes. In the meantime, microtubules were destroyed in the cells treated with either nocodazole or the compound of the present invention, indicating that chromosome concentration was incomplete (see FIG. 7).

When the said compound was treated to HeLa cells, all the microtubules were destroyed at the concentration of 1 μM. The lower concentration than 1 μM could inhibit the functions of microtubule, so that chromosomes could not be successfully divided (see FIG. 8).

To identify the binding site of ethyl(2-methyl-3{(E)-[(naphtho[2,1-b]furan-2-ylcarbonyl)hydrazono]methyl}-1H-indole-1-yl)acetate in tubulin, tubulin binding mode of the compound was set up with X-ray structure PDB code 1SAO by computer modeling, followed by analysis. As a result, it was confirmed that the compound was conjugated to the site between α and β subunit of tubulin (see FIG. 9).

To investigate the anticancer activity of ethyl(2-methyl-3{(E)-[(naphtho[2,1-b]furan-2-ylcarbonyl)hydrazono]

methyl}-1H-indole-1-yl)acetate and cholchicine in the FVB/N mouse induced with cancer by using DMBA/TPA, DMBA was first treated to FVB/N mouse to induce tumor. Then, TPA was treated to the mouse to promote the tumor growth. Group 1: DMBA and acetone treated group (negative control), group 2: DMBA and TPA treated group (positive control), group 3: the group treated with cholchicine after being treated with DMBA/TPA (experimental group 1); and group 4: the group treated with the said compound after being treated with DMBA/TPA (experimental group 2) were prepared. In the experimental groups treated with cholchicine and the said compound, the number of skin tumor was significantly decreased (see FIG. 10).

To investigate the number and the size of tumor in the FVB/N mouse induced with skin tumor by the treatment of ethyl(2-methyl-3{(E)-[(naphtho[2,1-b]furan-2-ylcarbonyl)hydrazono]methyl}-1H-indole-1-yl)acetate and cholchicine, each mouse group was treated with different materials and the number and the volume of tumor of each group were observed for 15 weeks. As a result, the compound above and cholchicine were confirmed to have a significant anti-cancer activity in the mouse group induced with skin cancer by using DMBA/TPA (see FIG. 11).

The FVB/N mouse model induced with skin tumor was treated with ethyl(2-methyl-3{(E)-[(naphtho[2,1-b]furan-2-ylcarbonyl)hydrazono]methyl}-1H-indole-1-yl)acetate and cholchicine and then the number of mouse that still had tumor was counted. Particularly, each mouse group was treated with different materials, followed by observation for 15 weeks. The tumor generation rate was presented as %. As a result, a tumor (2 mm) began to be formed in the positive control from $8^{th}$ week from the treatment, which reached 100% at week #10. In the meantime, the tumor generation in the experimental group treated with cholchicine or the above compound was inhibited until week #9 or week #10 (see FIG. 12).

The FVB/N mouse induced with skin tumor was treated with DMBA and then the average weight of tumors generated in there was observed and measured for 15 weeks. The weight of the tumor generated in the experimental group treated with cholchicine or the compound above was significantly lower than that of the positive control. The average weight of tumors generated in the experimental group 2 treated with the compound of the present invention was only $\frac{1}{10}$ times the weight of the positive control (see FIG. 13).

Therefore, ethyl(2-methyl-3{(E)-[(naphtho[2,1-b]furan-2-ylcarbonyl)hydrazono]methyl}-1H-indole-1-yl)acetate, the novel mitosis inhibitor of the present invention, not only induces apoptosis by inhibiting tubulin polymerization in the course of mitosis but also displays an excellent anticancer effect in the multi-drug resistant cancer cells, so that it can be effectively used for the treatment of cell proliferative disease including various cancers.

The composition comprising ethyl(2-methyl-3{(E)-[(naphtho[2,1-b]furan-2-ylcarbonyl)hydrazono]methyl}-1H-indole-1-yl)acetate of the present invention can include, in addition to the compound, at least one of active ingredients having the same or similar functions to the same.

The composition of the present invention can additionally include a pharmaceutically acceptable additive, which is exemplified by starch, gelatinized starch, microcrystalline cellulose, lactose, povidone, colloidal silicon dioxide, calcium hydrogen phosphate, lactose, mannitol, taffy, Arabia rubber, pregelatinized starch, corn starch, cellulose powder, hydroxypropyl cellulose, Opadry, sodium carboxy methyl starch, carunauba wax, synthetic aluminum silicate, stearic acid, magnesium stearate, aluminum stearate, calcium stearate, white sugar, dextrose, sorbitol, talc, etc. The pharmaceutically acceptable additive herein is preferably added by 0.1~90 weight part to the composition.

The composition of the present invention can be administered orally or parenterally and be used in general forms of pharmaceutical formulation. The composition of the present invention can be prepared for oral or parenteral administration by mixing with generally used diluents or excipients such as fillers, extenders, binders, wetting agents, disintegrating agents and surfactant. Solid formulations for oral administration are tablets, pills, powders, granules and capsules. These solid formulations are prepared by mixing the compound with one or more suitable excipients such as starch, calcium carbonate, sucrose or lactose, gelatin, etc. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions, emulsions, lyophilized preparations, suppositories and injections. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerogelatin, etc.

The composition of the present invention can be administered orally or parenterally. The parenteral administration includes skin external administration, intraperitoneal injection, intrarectal injection, subcutaneous injection, intravenous injection, intramuscular injection and intrathoracic injection. The effective dosage of the composition can be determined according to weight, age, gender, health condition, diet, administration frequency, administration method, excretion and severity of disease.

The composition of the present invention is administered at the pharmaceutically effective dose. The term "pharmaceutically effective dose" herein indicates the amount enough to treat the disease with applicable, reasonable or risky concentration. The dose can be determined by considering many factors such as the type of inflammatory disease, severity of the disease, activity of the drug, sensitivity to the drug, administration frequency and pathway, excretion, term of treatment, co-treatment drug and other factors regarded as relevant in the medicinal field. The composition of the present invention can be administered alone or together with other therapeutic agents. It can be co-treated or treated stepwise with the conventional therapeutic agents in a single or multiple units. Considering all the factors above, it is important to treat the compound in order to get a maximum effect with a minimum amount without side effects, and a preferable dose can be determined by those in the art.

Particularly, the effective dose of the compound of the present invention can be determined according to age, gender, and weight of a patient. The effective dose is preferably 0.1~100 mg/kg, and more preferably 0.5~10 mg/kg, which can be administered everyday or every other day, 1~3 times a day. However, the dose can be increased or decreased according to administration pathway, condition, gender, weight, and age, so the proposed dose cannot limit the scope of the present invention in any way.

The present invention also provides a health food for the prevention and improvement of cell proliferative disease comprising ethyl(2-methyl-3{(E)-[(naphtho[2,1-b]furan-2-ylcarbonyl)hydrazono]methyl}-1H-indole-1-yl)acetate represented by the below formula 1 or the pharmaceutically acceptable salts thereof as an active ingredient:

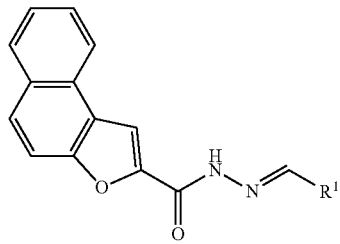

[Formula 1]

(In the formula 1, R¹ is

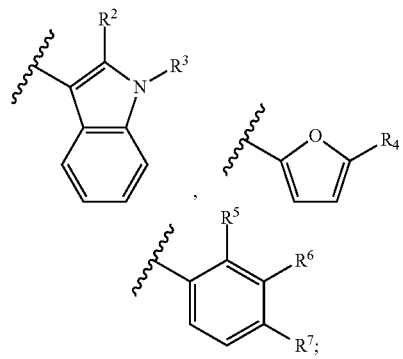

$R^2$ is hydrogen, or $C_{1-5}$ straight or branched alkyl;
$R^3$ is hydrogen, $C_{1-5}$ straight or branched alkyl,

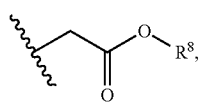

$C_{1-5}$ straight or branched alkenyl, or $C_{1-5}$ straight or branched cyanoalkyl, wherein $R^8$ is $C_{1-5}$ straight or branched alkyl;

$R^4$ is nitro, or

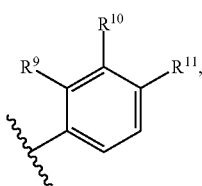

wherein $R^9$, $R^{10}$ and $R^{11}$ are independently hydrogen, halogen, nitro, or $C_{1-5}$ straight or branched alkyl;

$R^5$, $R^6$ and $R^7$ are independently hydrogen, hydroxy, $C_{1-5}$ straight or branched alkoxy, or $C_{1-5}$ straight or branched phenylalkoxy).

The compound represented by the above formula 1 can be selected from the group consisting of the compounds represented by the below formula 2~formula 12, but not always limited thereto:

[Formula 2]

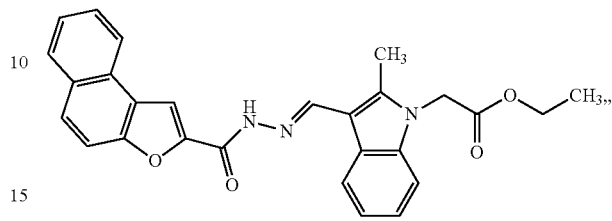

[Formula 3]

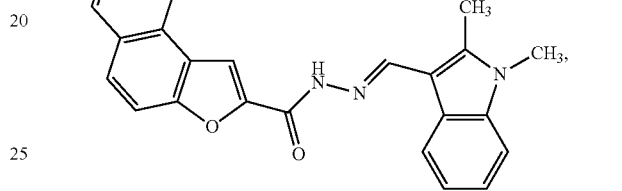

[Formula 4]

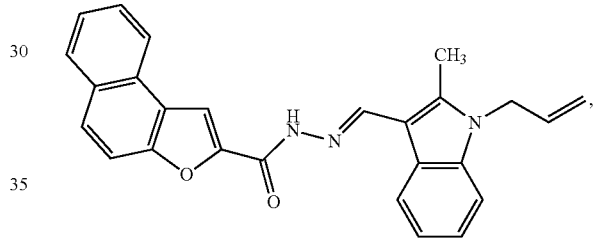

[Formula 5]

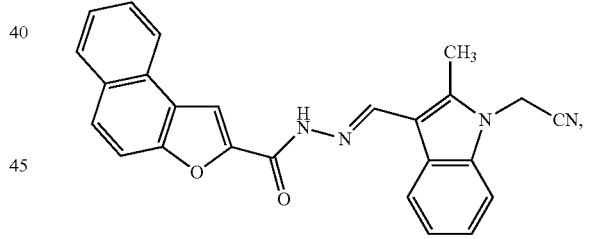

[Formula 6]

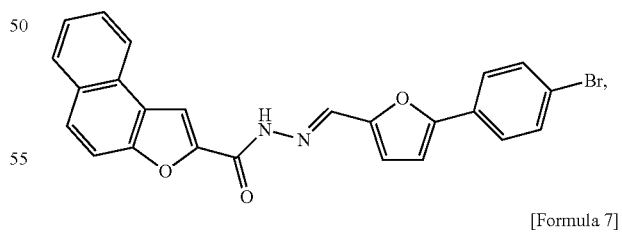

[Formula 7]

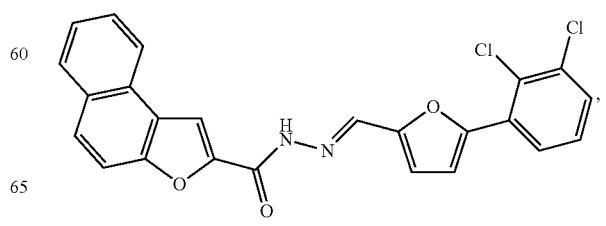

-continued

[Formula 8]
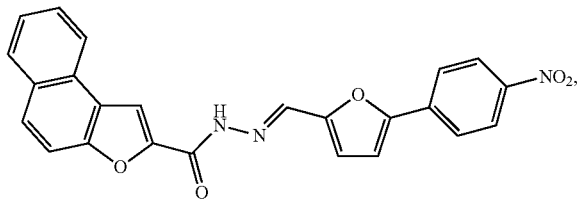

[Formula 9]
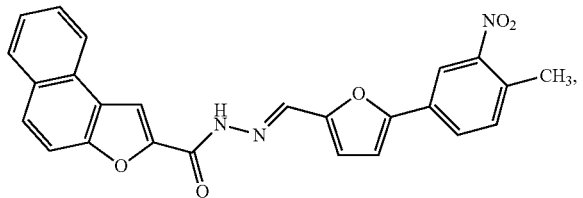

[Formula 10]
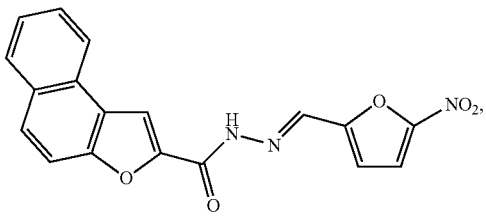

[Formula 11]
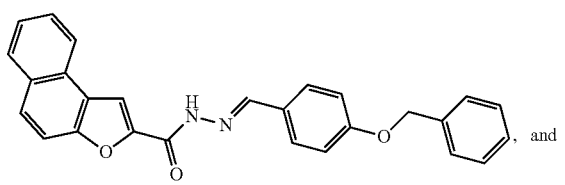, and

[Formula 12]
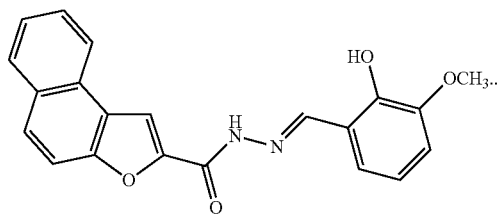

The novel mitosis inhibitor of the present invention, ethyl(2-methyl-3{(E)-[(naphtho[2,1-b]furan-2-ylcarbonyl) hydrazono]methyl}-1H-indole-1-yl)acetate, induces apoptosis by inhibiting tubulin polymerization in the course of mitosis and displays an excellent anticancer effect in the multi-drug resistant cancer cells, so that it can be effectively used for the prevention and improvement of cell proliferative disease including various cancers.

The compound represented by formula 1 of the present invention can be used as the form of a pharmaceutically acceptable salt, in which the salt is preferably acid addition salt formed by pharmaceutically acceptable free acids. The acid addition salt can be obtained from inorganic acids such as hydrochloric acid, nitric acid, phosphoric acid, sulfuric acid, hydrobromic acid, hydroiodic acid, nitrous acid and phosphorous acid, or non-toxic organic acids such as aliphatic mono/dicarboxylate, phenyl-substituted alkanoate, hydroxy alkanoate, alkandioate, aromatic acids and aliphatic/aromatic sulfonic acids. The pharmaceutically non-toxic salts are exemplified by sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, cabacate, fumarate, maliate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, hydroxybutylate, glycolate, malate, tartrate, methanesulfonate, propanesulfonate, naphtholene-1-sulfonate, naphtholene-2-sulfonate and mandelate.

The acid addition salt in this invention can be prepared by the conventional method known to those in the art. For example, the compound of formula 1 is dissolved in an organic solvent such as methanol, ethanol, acetone, methylenechloride, or acetonitrile, to which organic acid or inorganic acid is added to induce precipitation. Then, the precipitate is filtered and dried to give the salt. Or the solvent and the excessive acid are distillated under reduced pressure, and the residue is dried to give the salt. Or the precipitate is crystallized in the organic solvent to give the same.

A pharmaceutically acceptable metal salt can be prepared by using a base. Alkali metal or alkali earth metal salt is obtained by the following processes: dissolving the compound in excessive alkali metal hydroxide or alkali earth metal hydroxide solution; filtering non-soluble compound salt; evaporating the remaining solution and drying thereof. At this time, the metal salt is preferably prepared in the pharmaceutically suitable form of sodium, potassium, or calcium salt. And the corresponding silver salt is prepared by the reaction of alkali metal or alkali earth metal salt with proper silver salt (ex; silver nitrate).

The present invention further provides a method for treating cancer containing the step of administering a pharmaceutically effective dose of ethyl(2-methyl-3{(E)-[(naphtho[2,1-b]furan-2-ylcarbonyl)hydrazono]methyl}-1H-indole-1-yl)acetate or the pharmaceutically acceptable salts thereof to a subject having cell proliferative disease:

[Formula 1]
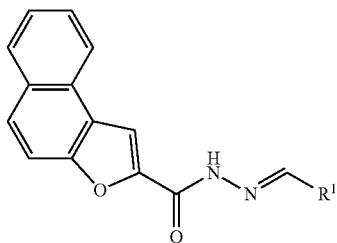

(In the formula 1,
R$^1$ is

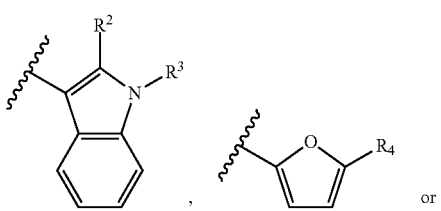

or (In the formula 1,

R¹ is

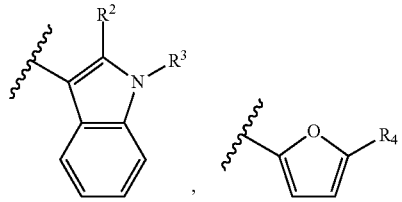

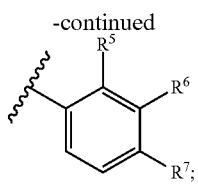

R² is hydrogen, or $C_{1-5}$ straight or branched alkyl;

R³ is hydrogen, $C_{1-5}$ straight or branched alkyl,

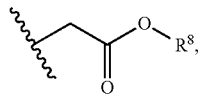
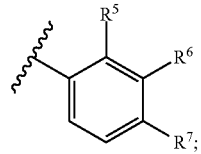

$C_{1-5}$ straight or branched alkenyl, or $C_{1-5}$ straight or branched cyanoalkyl, wherein $R^8$ is $C_{1-5}$ straight or branched alkyl;

R⁴ is nitro, or

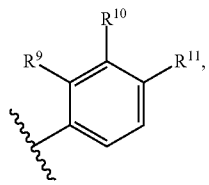
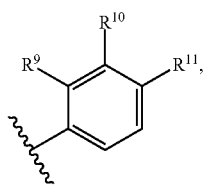

wherein $R^9$, $R^{10}$ and $R^{11}$ are independently hydrogen, halogen, nitro, or $C_{1-5}$ straight or branched alkyl;

$R^5$, $R^6$ and $R^7$ are independently hydrogen, hydroxy, $C_{1-5}$ straight or branched alkoxy, or $C_{1-5}$ straight or branched phenylalkoxy).

The novel mitosis inhibitor of the present invention, ethyl(2-methyl-3{(E)-[(naphtho[2,1-b]furan-2-ylcarbonyl)hydrazono]methyl}-1H-indole-1-yl)acetate, induces apoptosis by inhibiting tubulin polymerization in the course of mitosis and displays an excellent anticancer effect in the multi-drug resistant cancer cells, so that it can be effectively used for the treatment of cell proliferative disease including various cancers.

The present invention also provides a method for preventing cancer containing the step of administering a pharmaceutically effective dose of ethyl(2-methyl-3{(E)-[(naphtho[2,1-b]furan-2-ylcarbonyl)hydrazono]methyl}-1H-indole-1-yl)acetate or the pharmaceutically acceptable salts thereof to a subject:

[Formula 1]

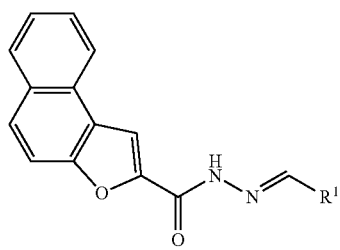

The novel mitosis inhibitor of the present invention, ethyl(2-methyl-3{(E)-[(naphtho[2,1-b]furan-2-ylcarbonyl)hydrazono]methyl}-1H-indole-1-yl)acetate, induces apoptosis by inhibiting tubulin polymerization in the course of mitosis and displays an excellent anticancer effect in the multi-drug resistant cancer cells, so that it can be effectively used for the prevention of cell proliferative disease including various cancers.

The present invention also provides a use of ethyl(2-methyl-3{(E)-[(naphtho[2,1-b]furan-2-ylcarbonyl)hydrazono]methyl}-1H-indole-1-yl)acetate or the pharmaceutically acceptable salts thereof for a pharmaceutical composition for the prevention and treatment of cell proliferative disease:

[Formula 1]

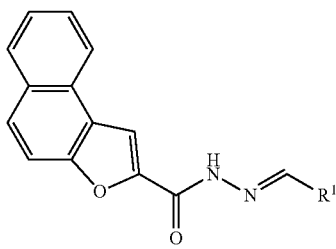

(In the formula 1,
R$^1$ is

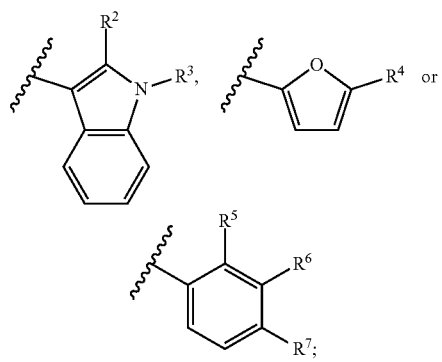

R$^2$ is hydrogen, or C$_{1-5}$ straight or branched alkyl;
R$^3$ is hydrogen, C$_{1-5}$ straight or branched alkyl,

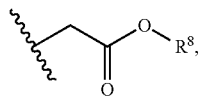

C$_{1-5}$ straight or branched alkenyl, or C$_{1-5}$ straight or branched cyanoalkyl, wherein R$^8$ is C$_{1-5}$ straight or branched alkyl;
R$^4$ is nitro, or

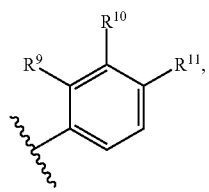

wherein R$^9$, R$^{10}$ and R$^{11}$ are independently hydrogen, halogen, nitro, or C$_{1-5}$ straight or branched alkyl;
R$^5$, R$^6$ and R$^7$ are independently hydrogen, hydroxy, C$_{1-5}$ straight or branched alkoxy, or C$_{1-5}$ straight or branched phenylalkoxy).

The novel mitosis inhibitor of the present invention, ethyl(2-methyl-3{(E)-[(naphtho[2,1-b]furan-2-ylcarbonyl)hydrazono]methyl}-1H-indole-1-yl)acetate, induces apoptosis by inhibiting tubulin polymerization in the course of mitosis and displays an excellent anticancer effect in the multi-drug resistant cancer cells, so that it can be effectively used for a composition for the prevention or treatment of cell proliferative disease including various cancers.

The present invention also provides a use of ethyl(2-methyl-3{(E)-[(naphtho[2,1-b]furan-2-ylcarbonyl)hydrazono]methyl}-1H-indole-1-yl)acetate, the analogs thereof, or the pharmaceutically acceptable salts thereof for a health food for the prevention and improvement of cell proliferative disease:

[Formula 1]

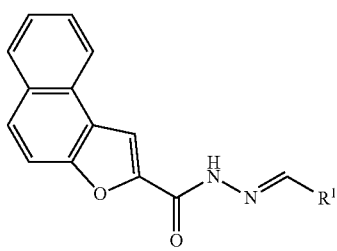

(In the formula 1,
R$^1$ is

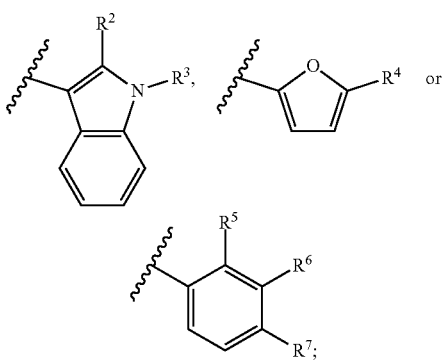

R$^2$ is hydrogen, or C$_{1-5}$ straight or branched alkyl;
R$^3$ is hydrogen, C$_{1-5}$ straight or branched alkyl,

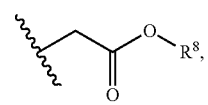

C$_{1-5}$ straight or branched alkenyl, or C$_{1-5}$ straight or branched cyanoalkyl, wherein R$^8$ is C$_{1-5}$ straight or branched alkyl;
R$^4$ is nitro, or

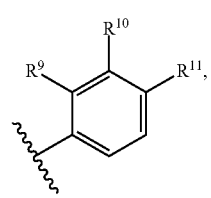

wherein R$^9$, R$^{10}$ and R$^{11}$ are independently hydrogen, halogen, nitro, or C$_{1-5}$ straight or branched alkyl;

$R^5$, $R^6$ and $R^7$ are independently hydrogen, hydroxy, $C_{1-5}$ straight or branched alkoxy, or $C_{1-5}$ straight or branched phenylalkoxy).

The novel mitosis inhibitor of the present invention, ethyl(2-methyl-3{(E)-[(naphtho[2,1-b]furan-2-ylcarbonyl)hydrazono]methyl}-1H-indole-1-yl)acetate, induces apoptosis by inhibiting tubulin polymerization in the course of mitosis and displays an excellent anticancer effect in the multi-drug resistant cancer cells, so that it can be effectively used for a health food for the prevention or improvement of cell proliferative disease including various cancers.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Anti-proliferative activity of ethyl(2-methyl-3{(E)-[(naphtho[2,1-b]furan-2-ylcarbonyl)hydrazono]methyl}-1H-indole-1-yl)acetate <1-1> Anti-proliferative activity of ethyl(2-methyl-3{(E)-[(naphtho[2,1-b]furan-2-ylcarbonyl)hydrazono]methyl}-1H-indole-1-yl)acetate analog compounds To investigate the anti-proliferative activity of the ethyl(2-methyl-3{(E)-[(naphtho[2,1-b]furan-2-ylcarbonyl)hydrazono]methyl}-1H-indole-1-yl)acetate analog compounds selected from the small molecule library, the following experiment was performed in order to determine which structure was responsible for such anti-proliferative activity.

Particularly, HeLa cell line (ATCC, USA) was treated with the compounds of Table 1 respectively, and then $IC_{50}$ (the half maximal inhibitory concentration) was investigated (Table 1).

As a result, as shown in Table 1, ethyl(2-methyl-3{(E)-[(naphtho[2,1-b]furan-2-ylcarbonyl)hydrazono]methyl}-1H-indole-1-yl)acetate, among all of those compounds, displayed the highest anti-proliferative activity. $IC_{50}$ of ethyl (2-methyl-3{(E)-[(naphtho[2,1-b]furan-2-ylcarbonyl)hydrazono]methyl}-1H-indole-1-yl)acetate was 0.26 μM, which indicated greater anti-proliferative activity than those of other analog compounds (0.44~5.4 μM). When acetate group conjugated to indole nitrogen in ethyl(2-methyl-3{(E)-[(naphtho[2,1-b]furan-2-ylcarbonyl)hydrazono]methyl}-1H-indole-1-yl)acetate was substituted with methyl group (compound A), the activity was two times decreased. When the acetate group was replaced with propene or acetonitryl (compound B, compound C), the anti-proliferative activity was decreased 8~10 times. When indole ring was replaced with furan (compounds D~H) or with phenyl group (compounds I and J), the anti-proliferative activity was decreased 9~15 times. Therefore, it was confirmed that ethyl(2-methyl-3{(E)-[(naphtho[2,1-b]furan-2-ylcarbonyl)hydrazono]methyl}-1H-indole-1-yl)acetate (STK899704) was a promising therapeutic agent candidate for cell proliferative disease (Table 1).

TABLE 1

| Compound | Formula | $IC_{50}$(μM) |
|---|---|---|
| STK899704 (Formula 2) | (E)-ethyl-(2-methyl-3-((2-(naphtho[2,1-b]furan-2carbonyl)methyl)-1H-indol-1-yl)acetate | 0.26 |
| A (Formula 3) | (E)-N'-(1,2-dimethyl-1H-indol-3-yl)methylene) naphtho[2,1-b]furan-2-carbohydrazide | 0.44 |

TABLE 1-continued

| Compound | Formula | IC$_{50}$(μM) |
|---|---|---|
| B (Formula 4) | 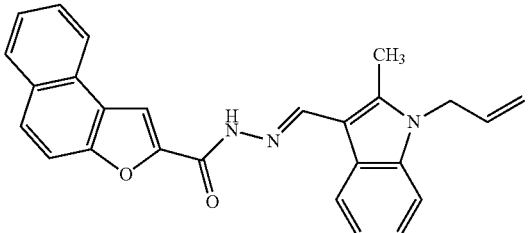 (E)-N'-((1-allyl-2-methyl-1H-indol-3-yl)methylene) naphtho[2,1-b]furan-2-carbohydrazide | 1.96 |
| C (Formula 5) | 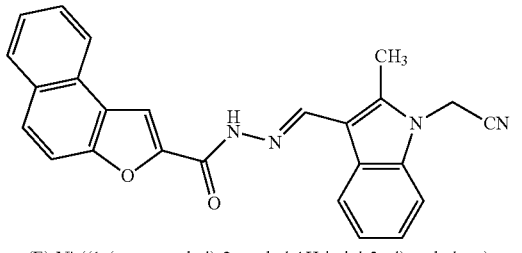 (E)-N'-((1-(cyanomethyl)-2-methyl-1H-indol-3-yl)methylene) naphtho[2,1-b]furan-2-carbohydrazide | 2.61 |
| D (Formula 6) | 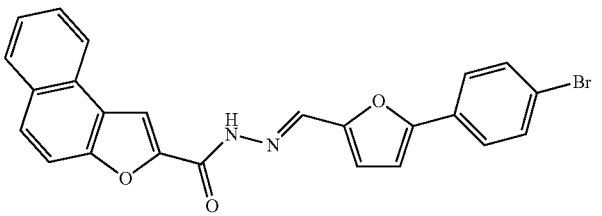 [SMILES: O=C(N/N=C/c1ccc(-c2ccc(Br)cc2)o1)c1cc2c(ccc3ccccc32)o1] (E)-N'-((5-(2,3-bromophenyl)furan-2-yl)methylene) naphtho[2,1-b]furan-2-carbohydrazide | 2.24 |
| E (Formula 7) | 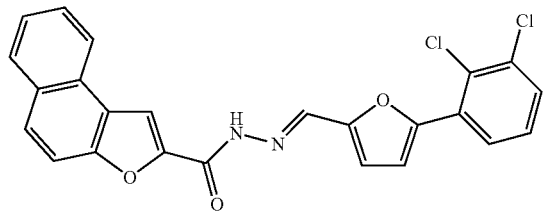 [SMILES: O=C(N/N=C/c1ccc(-c2cccc(Cl)c2Cl)o1)c1cc2c(ccc3ccccc32)o1] (E)-N'-((5-2,3-dichlorophenyl)furan-2-yl)methylene) naphtho[2,1-b]furan-2-carbohydrazide | 2.61 |
| F (Formula 8) | 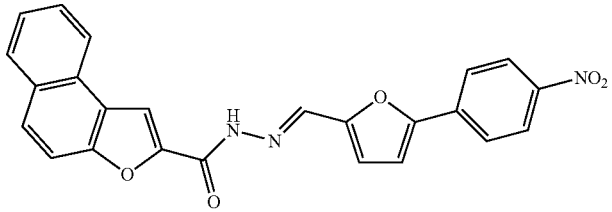 [SMILES: O=C(N/N=C/c1ccc(-c2ccc([N+](=O)[O-])cc2)o1)c1cc2c(ccc3ccccc32)o1] (E)-N'-((5-(4-nitrophenyl)furan-2-yl)methylene) naphtho[2,1-b]furan-2-carbohydrazide | 2.88 |

TABLE 1-continued

| Compound | Formula | IC$_{50}$(µM) |
|---|---|---|
| G (Formula 9) | 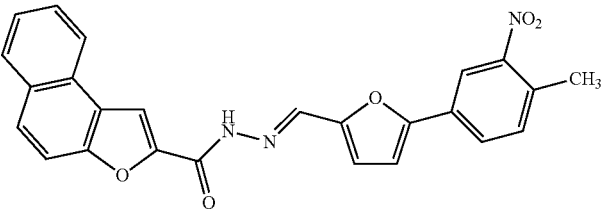 [SMILES: Cc1ccc(-c2ccc(/C=N/NC(=O)c3cc4c(ccc5ccccc54)o3)o2)cc1[N+](=O)[O-]]<br>(E)-N'-((5-(4-methyl-3-nitrophenyl)furan-2-yl)methylene) naphtho[2,1-b]furan-2-carbohydrazide | 3.11 |
| H (Formula 10) | 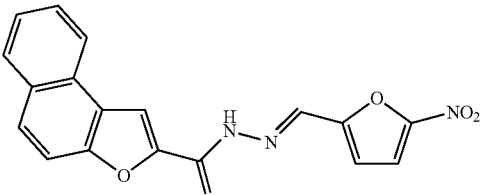<br>(E)-N'-((5-nitrofuran-2-yl)methylene) naphtho[2,1-b]furan-2-carbohydrazide | 5.4 |
| I (Formula 11) | 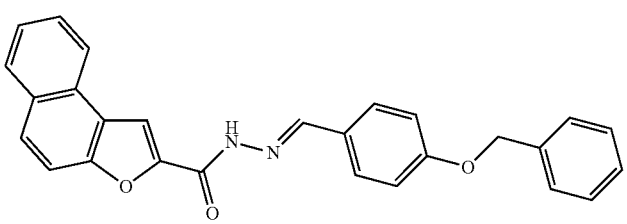 [SMILES: O=C(N/N=C/c1ccc(OCc2ccccc2)cc1)c1cc2c(ccc3ccccc32)o1]<br>(E)-N'-(4-(benzyloxy)benzylidene) naphtho[2,1-b]furan-2-carbohydrazide | 3.67 |
| J (Formula 12) | 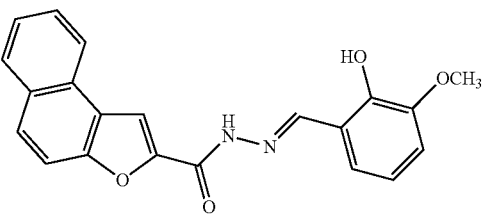 [SMILES: COc1cccc(/C=N/NC(=O)c2cc3c(ccc4ccccc43)o2)c1O]<br>(E)-N'-(2-hydroxy-3-methoxybenzylidene) naphtho[2,1-b]furan-2-carbohydrazide | 3.97 |

<1-2> Anti-proliferative activity of ethyl(2-methyl-3{(E)-[(naphtho[2,1-b]furan-2-ylcarbonyl)hydrazono]methyl}-1H-indole-1-yl)acetate HeLa cells were treated with 100 nM, 250 nM, 500 nM and 1 µM of ethyl(2-methyl-3{(E)-[(naphtho[2,1-b]furan-2-ylcarbonyl)hydrazono]methyl}-1H-indole-1-yl)acetate or DMSO for 4 days. Then, the cell growth was confirmed by MTT assay. All the obtained numbers were calculated by normalizing the value of Day 0. The data presents the mean value obtained from the assay performed in triplicate.

Particularly, HeLa cells were distributed in a 96-well plate at the density of 2×10$^3$ cells/well. The cells were treated with DMSO or the compound of the present invention, to which MTT reagent was added at the concentration of 10 µl/well. 2 hours later, OD$_{450}$ was measured, which became the value of Day 0. 4 days later, MTT reagent was added thereto again. 2 hours later, OD$_{450}$ was measured. The data presents the mean value obtained from the assay performed in triplicate. As a result, as shown in FIG. 1, ethyl(2-methyl-3{(E)-[(naphtho[2,1-b]furan-2-ylcarbonyl)hydrazono]methyl}-1H-indole-1-yl)acetate inhibited HeLa cell growth dose-dependently, and at this time IC$_{50}$ was 260 nM (FIG. 1).

Example 2

Confirmation of anti-proliferative effect of ethyl(2-methyl-3{(E)-[(naphtho[2,1-b]furan-2-ylcarbonyl) hydrazono]methyl}-1H-indole-1-yl)acetate <2-1> Anti-proliferative effect of ethyl(2-methyl-3{(E)-[(naphtho[2,1-b]furan-2-ylcarbonyl)hydrazono]methyl}-1H-indole-1-yl)acetate on various cancers The following experiment was performed to investigate whether or not ethyl(2-methyl-3{(E)-[(naphtho[2,1-b]furan-2-ylcarbonyl)hydrazono]methyl}-1H-indole-1-yl)acetate had the anti-proliferative activity in other types of cancer cells than HeLa (uterine cervical cancer cell line).

Various cancer cell lines (rectal cancer, prostate cancer, breast cancer, lung cancer, stomach cancer, liver cancer, leukemia, brain cancer, and glioma cell lines) were cultured in microtiter plate (1-3×10³ cells/well), to which ethyl(2-methyl-3{(E)-[(naphtho[2,1-b]furan-2-ylcarbonyl)hydrazono]methyl}-1H-indole-1-yl)acetate was treated. The culture continued for 4 days. Cytotoxicity was investigated by MTT assay by the same manner as described in Example <1-2>. IC$_{50}$ was calculated by long-dose response curve. The data presents the mean value obtained from the assay performed in triplicate.

As a result, as shown in Table 2, ethyl(2-methyl-3{(E)-[(naphtho[2,1-b]furan-2-ylcarbonyl)hydrazono]methyl}-1H-indole-1-yl)acetate inhibited cell growth in the cell lines of uterine cervical cancer, rectal cancer, prostate cancer, breast cancer, lung cancer, stomach cancer, liver cancer, leukemia, brain cancer, and glioma. At this time, IC$_{50}$ was as excellent as 0.22~1.06 μM (Table 2).

TABLE 2

| Cell line | Tumor origin site | IC$_{50}$ (nM) |
|---|---|---|
| HeLa | Cervix | 260 |
| Hep3B | Liver | 683 |
| HepG2 | Liver | 820 |
| HCT116 | Large intestine | 717 |
| HT-29 | Large intestine | 701 |
| PC-3 | Prostate | 650 |
| A549 | Lung | 843 |
| NCI-H460 | Lung | 806 |
| MDA-MB-231 | Breast | 543 |
| SNU-484 | Stomach | 221 |
| SNU-601 | Stomach | 773 |
| HL60 | Blood | 563 |
| A-172 | Brain | 603 |
| SNB-75 | Brain | 588 |
| U373MG | Brain | 517 |

Example 3

Confirmation of anti-proliferative effect of ethyl(2-methyl-3{(E)-[(naphtho[2,1-b]furan-2-ylcarbonyl)hydrazono]methyl}-1H-indole-1-yl)acetate on various cancer cell lines showing multi-drug resistance The following experiment was performed to investigate whether or not ethyl(2-methyl-3{(E)-[(naphtho[2,1-b]furan-2-ylcarbonyl)hydrazono]methyl}-1H-indole-1-yl)acetate had the anti-proliferative effect on those cancer cell lines showing multi-drug resistance.

Particularly, K562, MCF7 (Bio-Evaluation Center, Korea Research Institute of Bioscience and Biotechnology, Korea), and the multi-drug resistant cell lines thereof, K562/ADR and MCF7/ADR (Bio-Evaluation Center, Korea Research Institute of Bioscience and Biotechnology, Korea) were cultured in microtiter plate (1-3×10³ cells/well). Then, the cells were treated with ethyl(2-methyl-3{(E)-[(naphtho[2,1-b]furan-2-ylcarbonyl)hydrazono]methyl}-1H-indole-1-yl)acetate, doxorubicin, or taxol, followed by culture for 4 days. Cytotoxicity was investigated by MTT assay by the same manner as described in Example <1-2>. IC$_{50}$ was calculated by long-dose response curve. The data presents the mean value obtained from the assay performed in triplicate (Table 3).

The resistance factor of the multi-drug resistant cell line indicates the ratio of IC$_{50}$ of the multi-drug resistant cell line to IC$_{50}$ of the parent cell line showing no resistance, which was presented as a number in the bracket.

As a result, as shown in Table 3, the resistance factor against doxorubicin and taxol in the multi-drug resistant cell line was 377~1584 times greater, indicating a strong resistance. However, the resistance factor against ethyl(2-methyl-3{(E)-[(naphtho[2,1-b]furan-2-ylcarbonyl)hydrazono]methyl}-1H-indole-1-yl)acetate was 0.2~0.6, suggesting that ethyl(2-methyl-3{(E)-[(naphtho[2,1-b]furan-2-ylcarbonyl)hydrazono]methyl}-1H-indole-1-yl)acetate had a stronger cytotoxicity effect on the multi-drug resistant cancer cell line (Table 3).

TABLE 3

| | IC$_{50}$ (μM) | | |
|---|---|---|---|
| Cell line | STK899704 | Doxorubicin | Taxol |
| K562 | 450 | 3.3 | 2 |
| K562/ADR | 285(0.6) | 3805(1153) | 1822(911) |
| MCF7 | 1060 | 53 | 4.3 |
| MCF7/ADR | 225(0.2) | 5230(98) | 1625(377) |

Example 4

Effect of ethyl(2-methyl-3{(E)-[(naphtho[2,1-b]furan-2-ylcarbonyl)hydrazono]methyl}-1H-indole-1-yl)acetate on cell cycle <4-1> Confirmation of Cell Number HeLa cells were treated with ethyl(2-methyl-3{(E)-[(naphtho[2,1-b]furan-2-ylcarbonyl)hydrazono]methyl}-1H-indole-1-yl)acetate for 17 hours, and then cell cycle distribution and mitotic index were investigated.

Particularly, HeLa cells were distributed in a 12-well plate at the density of 3×10⁴ cells/well, to which DMSO or the compound of the present invention was treated for 18 hours. Then, the cells were treated with propidium iodine dye to stain the cellular DNA, followed by FACS to investigate cell cycle. To calculate mitotic index, HeLa cells were distributed in a 12-well plate at the density of 3×10⁴ cells/well, to which DMSO or the compound of the present invention was treated for 18 hours. Then, the cells were treated with propidium iodine dye to stain the cellular DNA and alpha-tubulin, followed by observation under microscope. A specific phenomenon of mitosis was counted and the ratio was numerized. At this time, the thread like chromonema resulted from the DNA condensation in the course of mitosis and the spindle fibers made by alpha-tubulin were the two major key factors to determine the level of mitosis.

Figure 2:
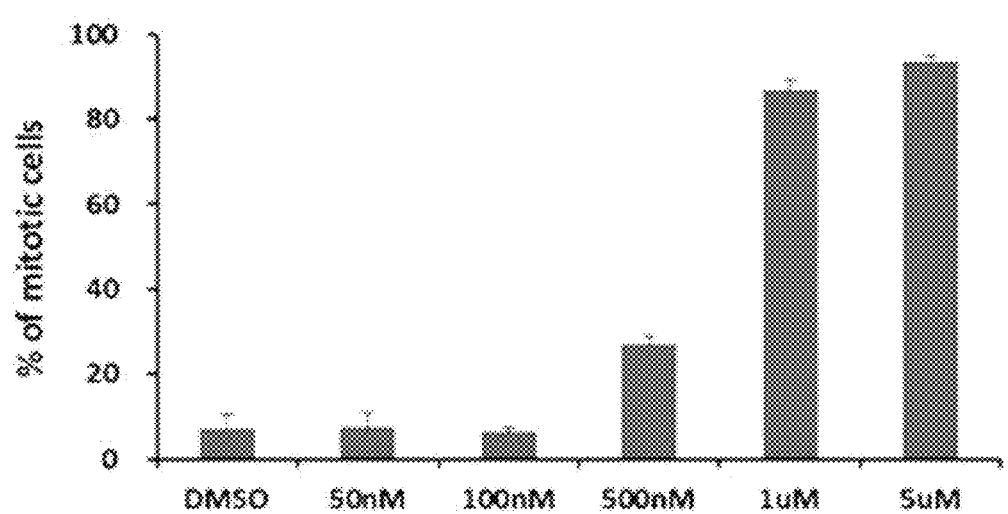
FIG. 2 is a diagram illustrating the result of counting the number of cells in each cell cycle by flow cytometry after treating ethyl(2-methyl-3{(E)-[(naphtho[2,1-b]furan-2-ylcarbonyl)hydrazono]methyl}-1H-indole-1-yl)acetate to HeLa cells.
Figure 3:
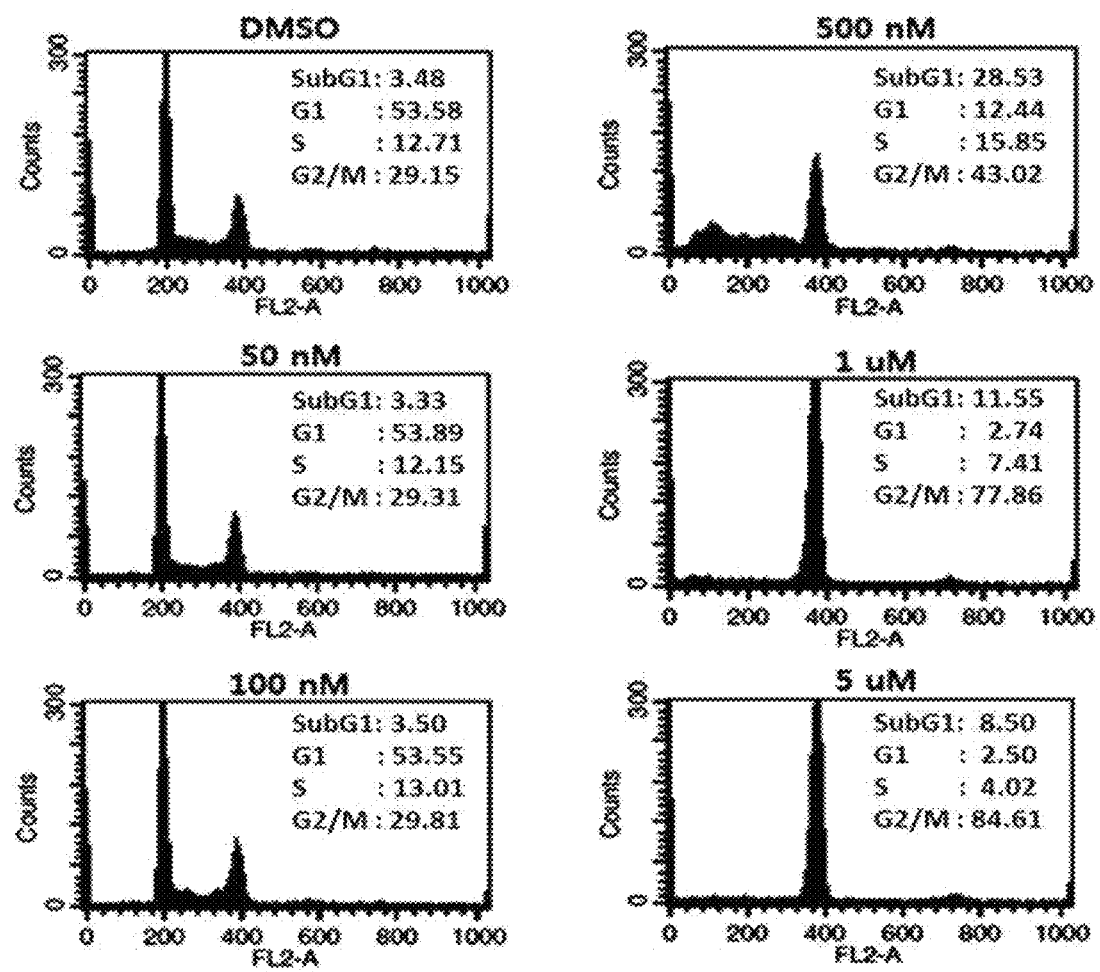
FIG. 3 is a diagram illustrating the increase of mitosis from about 30% to 80%, confirmed by counting the cells in the middle of mitosis after treating ethyl(2-methyl-3{(E)-[(naphtho[2,1-b]furan-2-ylcarbonyl)hydrazono]methyl}-1H-indole-1-yl)acetate to HeLa cells.

As a result, as shown in FIG. 2 and FIG. 3, the content of 4N DNA in G2/M phase was increased. When the cells were treated with ethyl(2-methyl-3{(E)-[(naphtho[2,1-b]furan-2-ylcarbonyl)hydrazono]methyl}-1H-indole-1-yl)acetate at the concentration of 0.5~1.0 μM, the number of the cells in G2/M phase was increased from 43% to 78% (FIG. 2).

At this time, mitotic cells like rounded cells were also increased. The number of the mitotic cells were counted. As a result, the mitotic index was increased from around 30% to around 80% (FIG. 3). The data presents the mean value obtained from the assay performed in triplicate. Error bar indicates standard deviation.

Therefore, it was confirmed that ethyl(2-methyl-3{(E)-[(naphtho[2,1-b]furan-2-ylcarbonyl)hydrazono]methyl}-1H-indole-1-yl)acetate arrested cell cycle in G2/M phase.

<4-2> Investigation of the effect of ethyl(2-methyl-3{(E)-[(naphtho[2,1-b]furan-2-ylcarbonyl)hydrazono]methyl}-1H-indole-1-yl)acetate on the proteins regulating cell division To investigate whether or not ethyl(2-methyl-3{(E)-[(naphtho[2,1-b]furan-2-ylcarbonyl)hydrazono]methyl}-

1H-indole-1-yl)acetate could inhibit cell division, the effect of ethyl(2-methyl-3{(E)-[(naphtho[2,1-b]furan-2-ylcarbonyl)hydrazono]methyl}-1H-indole-1-yl)acetate on the proteins regulating cell division was examined.

As the control for comparison, nocodazol, the well known depolymerizing agent, was used.

The effect of ethyl(2-methyl-3{(E)-[(naphtho[2,1-b]furan-2-ylcarbonyl)hydrazono]methyl}-1H-indole-1-yl)acetate on Cdc25C, Cyclin B1, and Plk1 (Polo-like kinase 1), the proteins regulating cell division, was investigated. When Cdc25C is activated in the course of cell division, Cdc25C is hyperphosphorylated so that its movement on SDS-PAGE is slowed down. Based on that principal, Cdc25C activation was investigated. Referring that the expressions of Cyclin B1 and Plk1 are differently regulated in each stage of cell cycle, the expression of each protein was measured. The levels of Cyclin B1 and Plk1 were the lowest in G1 phase. But Cyclin B1 and Plk1 began to be accumulated in S phase and the maximum levels of them were observed at the border of G2/M phase.

HeLa cells were treated with DMSO, nocodazole (NOC), or ethyl(2-methyl-3{(E)-[(naphtho[2,1-b]furan-2-ylcarbonyl)hydrazono]methyl}-1H-indole-1-yl)acetate for 17 hours. The cells were harvested, followed by immunoblotting using cyclin B1, Cdc25C, Plk1, and GAPDH specific antibodies. GAPDH was used as a loading control.

Figure 4:
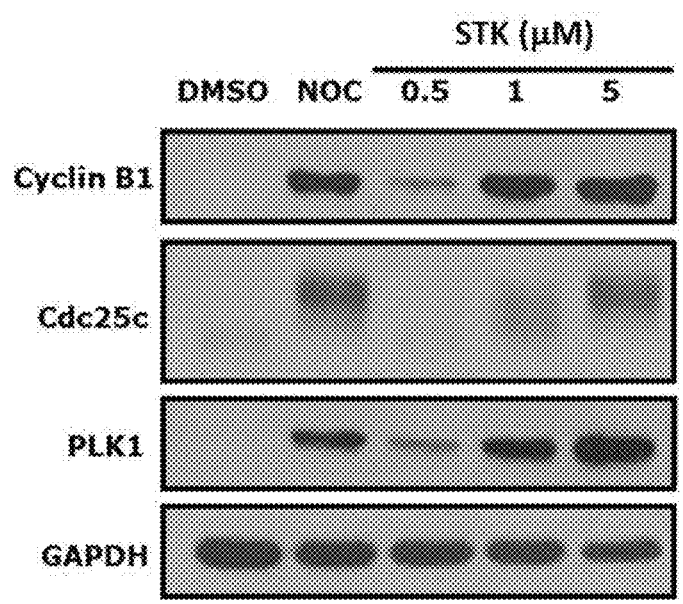
FIG. 4 is a diagram illustrating the effect of ethyl(2-methyl-3{(E)-[(naphtho[2,1-b]furan-2-ylcarbonyl)hydrazono]methyl}-1H-indole-1-yl)acetate on the proteins regulating cell cycle, confirmed by immunoblotting.

As a result, as shown in FIG. 4, Cdc25C was phosphorylated and cyclin B1 and Plk1 were accumulated in HeLa cells treated with ethyl(2-methyl-3{(E)-[(naphtho[2,1-b]furan-2-ylcarbonyl)hydrazono]methyl}-1H-indole-1-yl)acetate, which was consistent with the case of nocodazole treatment.

From the results obtained in Example <4-2>, it was confirmed that ethyl(2-methyl-3{(E)-[(naphtho[2,1-b]furan-2-ylcarbonyl)hydrazono]methyl}-1H-indole-1-yl)acetate arrested cell cycle in G2/M phase (FIG. 4).

Example 5

Investigation of apoptosis induced by ethyl(2-methyl-3{(E)-[(naphtho[2,1-b]furan-2-ylcarbonyl)hydrazono]methyl}-1H-indole-1-yl)acetate In the above Example 4, it was confirmed that ethyl(2-methyl-3{(E)-[(naphtho[2,1-b]furan-2-ylcarbonyl)hydrazono]methyl}-1H-indole-1-yl)acetate arrested mitosis. To confirm whether or not this arrest could induce apoptosis, the following experiment was performed.

Particularly, HeLa cells were treated with DMSO or ethyl(2-methyl-3{(E)-[(naphtho[2,1-b]furan-2-ylcarbonyl)hydrazono]methyl}-1H-indole-1-yl)acetate for 24 or 48 hours. Then, immunoblotting was performed to investigate the expressions of caspase-3 and PARP, the apoptosis related proteins. PARP (poly(ADP-ribose)polymerase) is one of the downstream cleavage proteins derived from caspase3. Immunoblotting was performed using caspase-3, PARP, and GAPDH specific antibodies.

Figure 5:
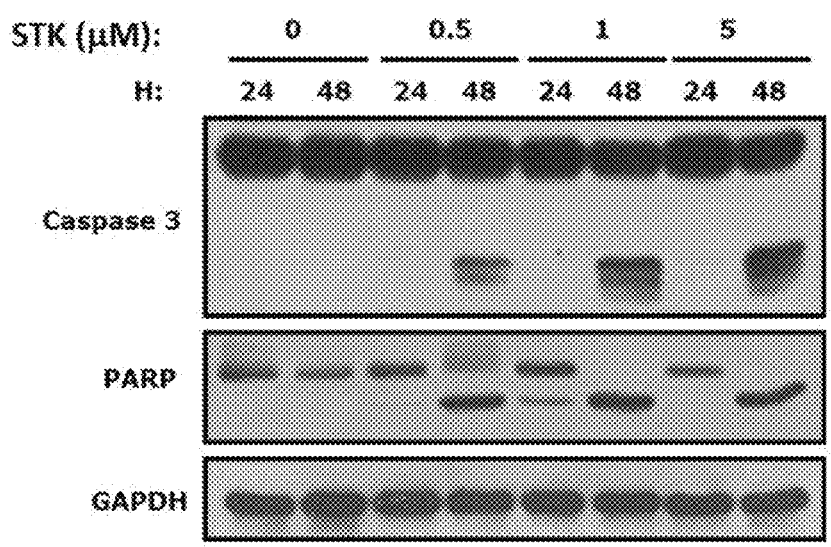
FIG. 5 is a diagram illustrating the effect of ethyl(2-methyl-3{(E)-[(naphtho[2,1-b]furan-2-ylcarbonyl)hydrazono]methyl}-1H-indole-1-yl)acetate on the proteins involved in apoptosis, confirmed by immunoblotting.

As a result, as shown in FIG. 5, caspase-3 cleavage was not observed within 24 hours from the treatment of ethyl (2-methyl-3{(E)-[(naphtho[2,1-b]furan-2-ylcarbonyl)hydrazono]methyl}-1H-indole-1-yl)acetate but was significantly increased 48 hours after the treatment of ethyl(2-methyl-3{(E)-[(naphtho[2,1-b]furan-2-ylcarbonyl)hydrazono]methyl}-1H-indole-1-yl)acetate at the concentration of 0.5 µM. The level of caspase-3 cleavage was more significantly increased when ethyl(2-methyl-3{(E)-[(naphtho[2,1-b]furan-2-ylcarbonyl)hydrazono]methyl}-1H-indole-1-yl)acetate was treated thereto at the concentration of 1 and 5 µM. This result indicates that ethyl(2-methyl-3{(E)-[(naphtho[2,1-b]furan-2-ylcarbonyl)hydrazono]methyl}-1H-indole-1-yl)acetate increased caspase-3 cleavage dose- and time-dependently. PARP cleavage was also significantly increased 48 hours after the addition of ethyl(2-methyl-3{(E)-[(naphtho[2,1-b]furan-2-ylcarbonyl)hydrazono]methyl}-1H-indole-1-yl)acetate to the cells.

Therefore, it was confirmed that ethyl(2-methyl-3{(E)-[(naphtho[2,1-b]furan-2-ylcarbonyl)hydrazono]methyl}-1H-indole-1-yl)acetate induced apoptosis (FIG. 5).

Example 6

Effect of ethyl(2-methyl-3{(E)-[(naphtho[2,1-b]furan-2-ylcarbonyl)hydrazono]methyl}-1H-indole-1-yl)acetate on tubulin polymerization The following experiment was performed to investigate the effect of ethyl(2-methyl-3{(E)-[(naphtho[2,1-b]furan-2-ylcarbonyl)hydrazono]methyl}-1H-indole-1-yl)acetate on the polymerization of tubulin.

<6-1> Degree of Turbidity

To measure the polymerization of tubulin in vitro, the buffer containing the purified tubulin and GTP was treated with ethyl(2-methyl-3{(E)-[(naphtho[2,1-b]furan-2-ylcarbonyl)hydrazono]methyl}-1H-indole-1-yl)acetate at the concentration of 5 µM. DMSO, and the equivalent Taxol and vinblastine were used as the controls. The polymerization of tubulin into microtubules was determined if the degree of turbidity was 340 nm.

Figure 6:
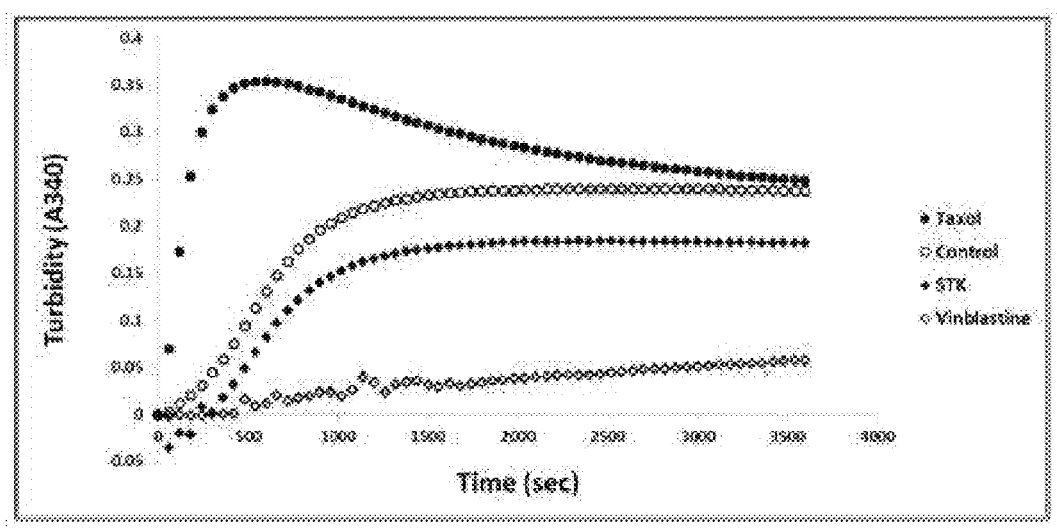
FIG. 6 is a diagram illustrating the effect of ethyl(2-methyl-3{(E)-[(naphtho[2,1-b]furan-2-ylcarbonyl)hydrazono]methyl}-1H-indole-1-yl)acetate on the polymerization of tubulin examined in vitro and presented by degree of turbidity.

As a result, as shown in FIG. 6, the degree of turbidity was lower when tubulin was treated with ethyl(2-methyl-3{(E)-[(naphtho[2,1-b]furan-2-ylcarbonyl)hydrazono]methyl}-1H-indole-1-yl)acetate than when treated with Taxol (FIG. 6).

<6-2> Chromosome Distribution

Figure 7:
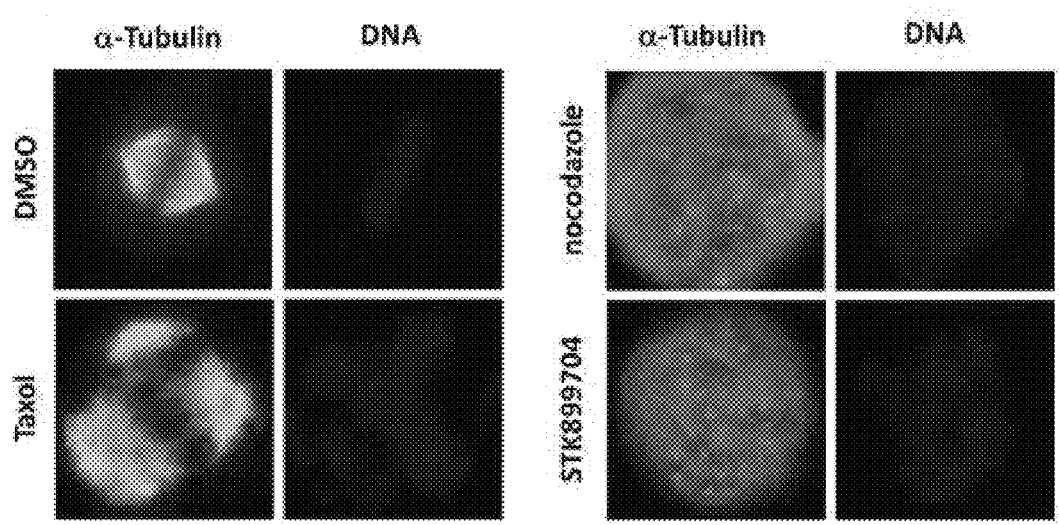
FIG. 7 is a diagram illustrating the effect of ethyl(2-methyl-3{(E)-[(naphtho[2,1-b]furan-2-ylcarbonyl)hydrazono]methyl}-1H-indole-1-yl)acetate on spindle fibers and chromosomes of the cell in the course of mitosis, examined by immunofluorescence and compared with the effects of taxol and nocodazol.

To investigate the effect of ethyl(2-methyl-3{(E)-[(naphtho[2,1-b]furan-2-ylcarbonyl)hydrazono]methyl}-1H-indole-1-yl)acetate on intracellular microtubules, HeLa cells were treated with DMSO, Taxol (100 µM), nocodazole (200 ng/ml), or ethyl(2-methyl-3{(E)-[(naphtho[2,1-b]furan-2-ylcarbonyl)hydrazono]methyl}-1H-indole-1-yl)acetate (5 µM) for 17 hours. After fixing the cells, the cells were immuno-stained with Alexa Fluor 488-conjugated anti-tubulin antibody and Hoechst 33342 to confirm α-tubulin and chromosomes. As a result, as shown in FIG. 7, Taxol strengthened the polymerization of tubulin so that multipolar spindle fibers with condensed chromosomes were produced. On the contrary, in the cells treated with nocodazole or ethyl(2-methyl-3{(E)-[(naphtho[2,1-b]furan-2-ylcarbonyl)hydrazono]methyl}-1H-indole-1-yl)acetate, chromosomes were not fully condensed and microtubules were destroyed (FIG. 7).

Figure 8:
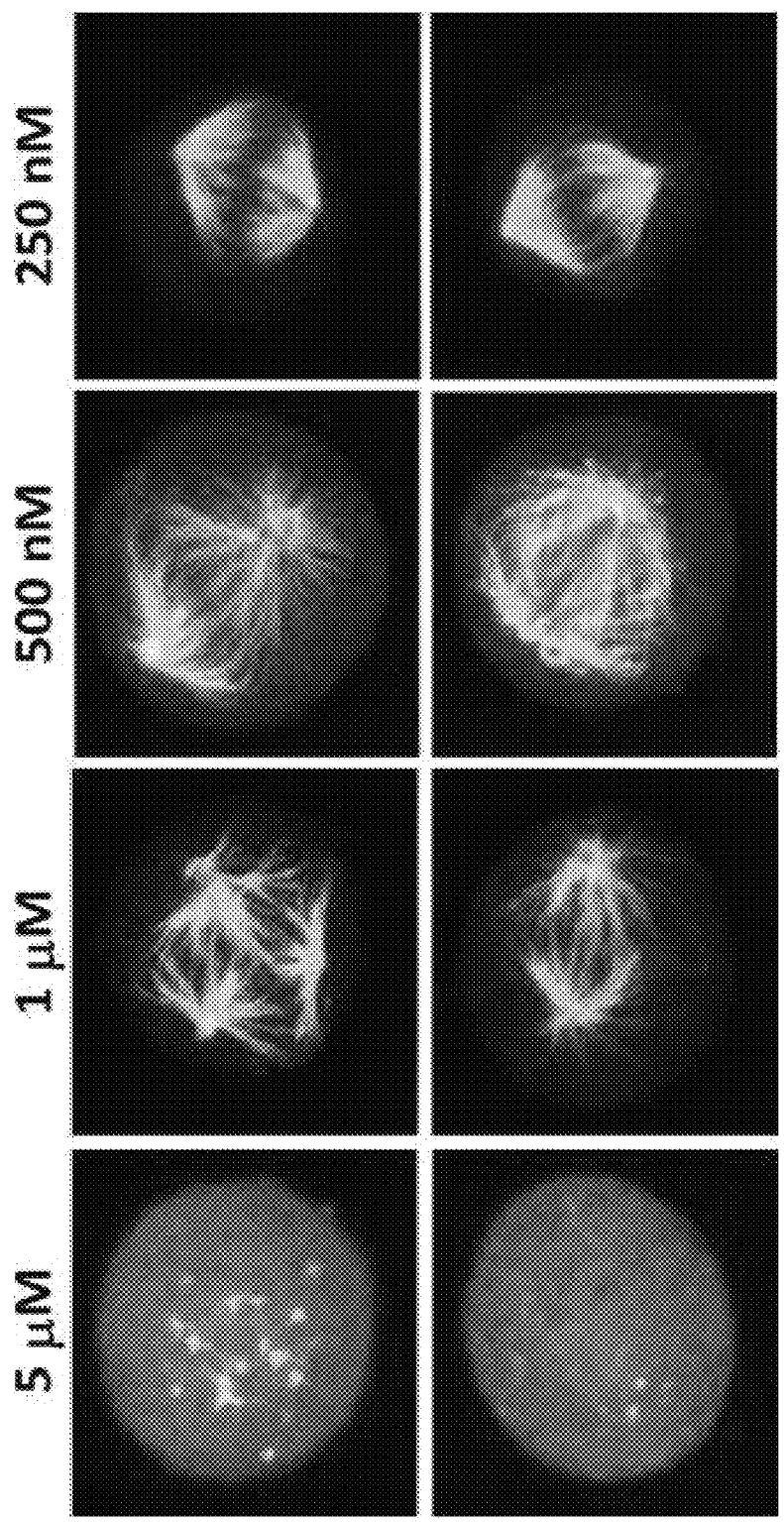
FIG. 8 is a diagram illustrating the effect of ethyl(2-methyl-3{(E)-[(naphtho[2,1-b]furan-2-ylcarbonyl)hydrazono]methyl}-1H-indole-1-yl)acetate on spindle fibers and chromosomes of the cell in the course of mitosis over the concentrations of the same, confirmed by immunofluorescence.

As shown in FIG. 8, when HeLa cells were treated with ethyl(2-methyl-3{(E)-[(naphtho[2,1-b]furan-2-ylcarbonyl)hydrazono]methyl}-1H-indole-1-yl)acetate, all the microtubules were destroyed at the concentration of 1 µM. Even with the lower concentration of ethyl(2-methyl-3{(E)-[(naphtho[2,1-b]furan-2-ylcarbonyl)hydrazono]methyl}-1H-indole-1-yl)acetate, microtubules were not able to be fully functioning and accordingly chromosomes could not be correctly divided (FIG. 8).

Therefore, it was confirmed that ethyl(2-methyl-3{(E)-[(naphtho[2,1-b]furan-2-ylcarbonyl)hydrazono]methyl}-1H-indole-1-yl)acetate was the material that could induce microtubule depolymerization.

Example 7

Confirmation of Binding Site

The following experiment was performed to confirm the tubulin binding site of ethyl(2-methyl-3{(E)-[(naphtho[2,1-b]furan-2-ylcarbonyl)hydrazono]methyl}-1H-indole-1-yl) acetate.

Particularly, a mode simulating the binding between ethyl (2-methyl-3{(E)-[(naphtho[2,1-b]furan-2-ylcarbonyl)hydrazono]methyl}-1H-indole-1-yl)acetate and tubulin was set up by using X-ray structure PDB code 1SA0 with computer modeling.

Figure 9:
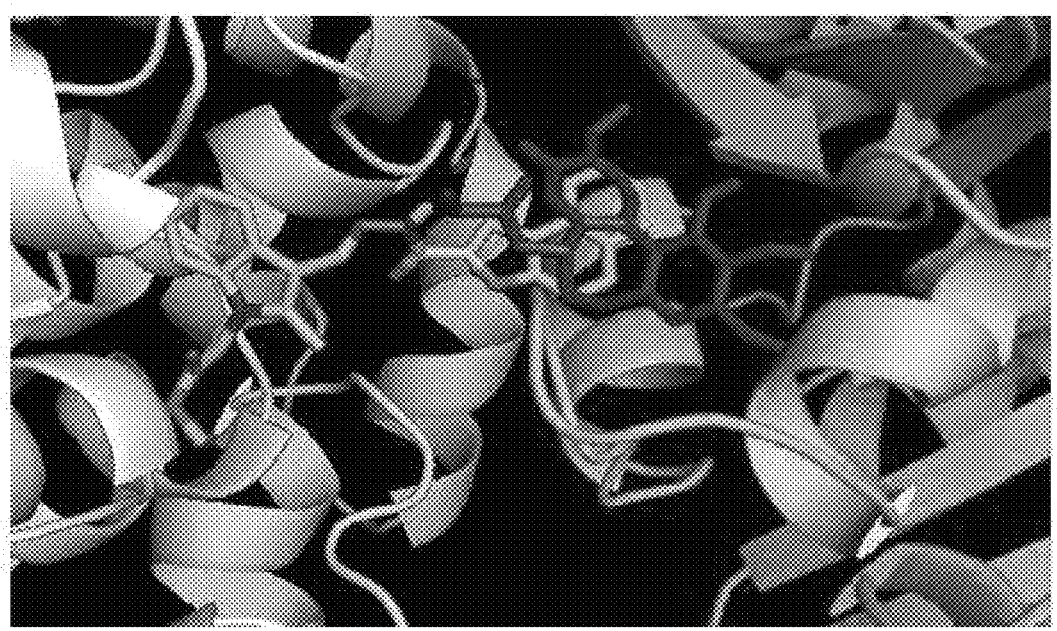
FIG. 9 is a diagram illustrating the binding site in tubulin where ethyl(2-methyl-3{(E)-[(naphtho[2,1-b]furan-2-ylcarbonyl)hydrazono]methyl}-1H-indole-1-yl)acetate would be conjugated, examined by computer modeling. The gray indicates α-subunit, and the blue indicates β-subunit.

As a result, as shown in FIG. 9, ethyl(2-methyl-3{(E)-[(naphtho[2,1-b]furan-2-ylcarbonyl)hydrazono]methyl}-1H-indole-1-yl)acetate was conjugated between α subunit and β subunit of tubulin (FIG. 9, rainbow rod). The cholchicine binding site was presented as the pink rod. From the above results, it was confirmed that ethyl(2-methyl-3{(E)-[(naphtho[2,1-b]furan-2-ylcarbonyl)hydrazono]methyl}-1H-indole-1-yl)acetate shared the tubulin binding site with the cholchicine binding site. Only cholchicine was bound to mainly β tubulin subunit, while ethyl(2-methyl-3{(E)-[(naphtho[2,1-b]furan-2-ylcarbonyl)hydrazono]methyl}-1H-indole-1-yl)acetate was bound to the site between tubulin dimer.

The above results indicate that ethyl(2-methyl-3{(E)-[(naphtho[2,1-b]furan-2-ylcarbonyl)hydrazono]methyl}-1H-indole-1-yl)acetate was bound to tubulin and the anti-proliferative activity of ethyl(2-methyl-3{(E)-[(naphtho[2,1-b]furan-2-ylcarbonyl)hydrazono]methyl}-1H-indole-1-yl)acetate was mainly attributed to the conjugation of ethyl (2-methyl-3{(E)-[(naphtho[2,1-b]furan-2-ylcarbonyl) hydrazono]methyl}-1H-indole-1-yl)acetate to tubulin, particularly to the cholchicine binding site.

Example 8

Investigation of anti-cancer effect of ethyl(2-methyl-3{(E)-[(naphtho[2,1-b]furan-2-ylcarbonyl) hydrazono]methyl}-1H-indole-1-yl)acetate and cholchicine in FVB/N mouse induced with cancer using DMBA/TPA <8-1> Raising the Test Mice and Grouping Thereof In this invention, the male FVB/N mice (6-7 weeks, Jackson Laboratory, USA) were raised under the condition of 12 hr bright lighting/12 hr dim lighting at the temperature of 24±2° C. with the humidity of 50±10% with water and feed provided freely. The care and process of the test animal was reviewed and approved by Institutional Animal Care and Use Committee (IACUC), Korea Research Institute of Bioscience and Biotechnology (KRIBB). DMBA (7,12-dimethylbenz[α]anthracene), TPA (12-O-tetradecanoylphorbol-13-acetate) and cholchicine were purchased from Sigma-Aldrich, and the synthesized ethyl(2-methyl-3{(E)-[(naphtho[2,1-b]furan-2-ylcarbonyl)hydrazono]methyl}-1H-indole-1-yl)acetate was provided from Dr. Thimmegowda.

<8-2> Construction of Mouse Model Induced with Skin Tumor and Investigation of Anticancer Effect The following experiment was performed to investigate the anticancer effect of ethyl(2-methyl-3{(E)-[(naphtho[2,1-b]furan-2-ylcarbonyl)hydrazono]methyl}-1H-indole-1-yl) acetate and cholchicine in the FVB/N mouse model induced with cancer.

Particularly, the dorsal skin of the said FVB/N mouse was shaved two days before the experiment. 100 μg of DMBA was added to 0.2 ml of acetone, which was treated to the mouse by single-local administration for 1 week to induce tumor. 5 fig of TPA was added to 0.2 ml of acetone, which was treated to the above mouse induced with tumor twice a day for 15 weeks to grow the tumor. 500 nM of ethyl(2-methyl-3{(E)-[(naphtho[2,1-b]furan-2-ylcarbonyl)hydrazono]methyl}-1H-indole-1-yl)acetate or cholchicine was dissolved in 0.2 ml of acetone, which was treated to the above mouse locally for 30 minutes each time for 15 weeks. Each group was composed of at least 10 mice and total 4 groups were prepared:

Group 1: DMBA and acetone treated group (negative control)

Group 2: DMBA and TPA treated group (positive control)

Group 3: DMBA/TPA and cholchicine treated group (experimental group 1)

Group 4: DMBA/TPA and ethyl(2-methyl-3{(E)-[(naphtho[2,1-b]furan-2-ylcarbonyl)hydrazono]methyl}-1H-indole-1-yl)acetate treated group (experimental group 2).

In addition, skin tumor such as papilloma was checked every week during the whole period of experiment. The tumor in the size of at least 2 mm was judged as positive. 15 weeks later, the mice were sacrificed with $CO_2$. The skin tumor was extracted for histopathological/biochemical analysis.

Figure 10:
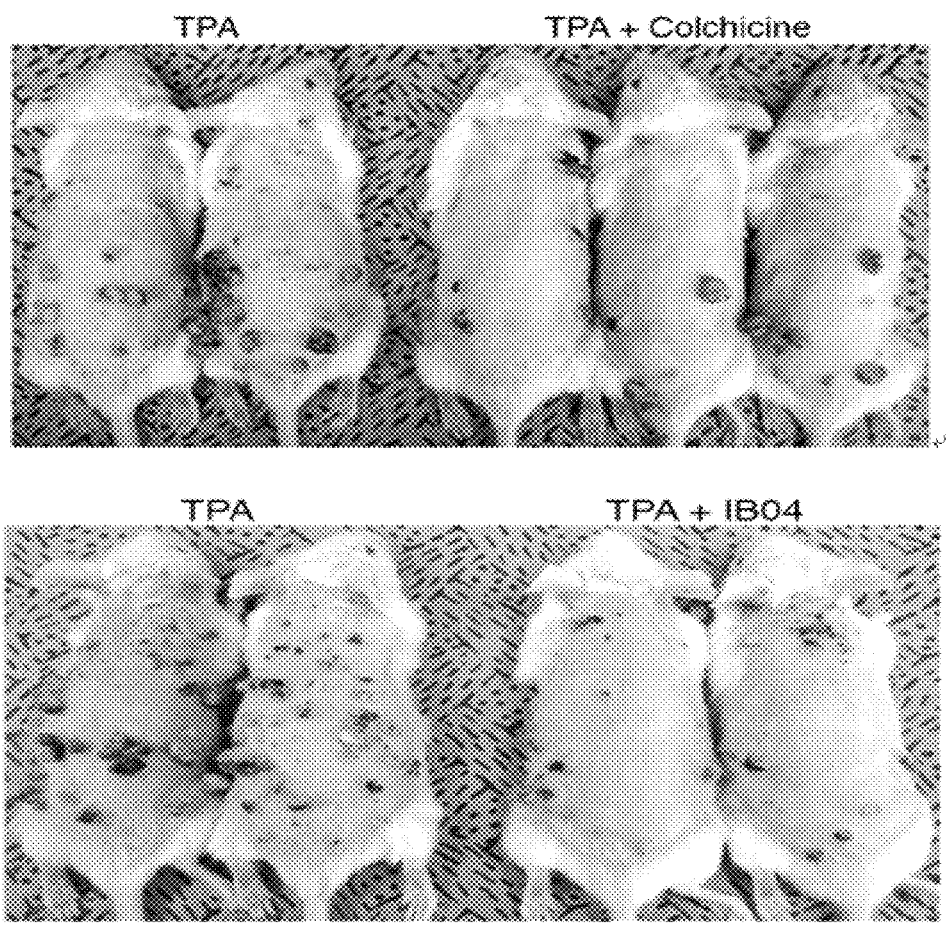
FIG. 10 is a diagram illustrating the counting of the number of skin tumors in the FVB/N mouse induced with skin tumor after treating the mouse with ethyl(2-methyl-3{(E)-[(naphtho[2,1-b]furan-2-ylcarbonyl)hydrazono]methyl}-1H-indole-1-yl)acetate and cholchicine.
A: TPA treated group;
B: TPA+cholchicine treated group; and
C: TPA+ethyl(2-methyl-3{(E)-[(naphtho[2,1-b]furan-2-ylcarbonyl)hydrazono]methyl}-1H-indole-1-yl)acetate treated group.

As a result, as shown in FIG. 10, in the experimental group treated with ethyl(2-methyl-3{(E)-[(naphtho[2,1-b]furan-2-ylcarbonyl)hydrazono]methyl}-1H-indole-1-yl)acetate and cholchicine, the number of skin tumor was significantly reduced (FIG. 10).

<8-3> Investigation of the number and the size of skin tumor in the FVB/N mouse induced with skin tumor after the treatment of ethyl(2-methyl-3{(E)-[(naphtho[2,1-b]furan-2-ylcarbonyl)hydrazono] methyl}-1H-indole-1-yl)acetate and cholchicine The number and the volume of the skin tumor induced in the mouse groups treated with different materials by the same manner as described in Example <8-2> were observed for 15 weeks.

Particularly, tumors were observed in each mouse group and the data were recorded for 15 weeks. The average number and the volume of tumor in each group were calculated.

Figure 11:
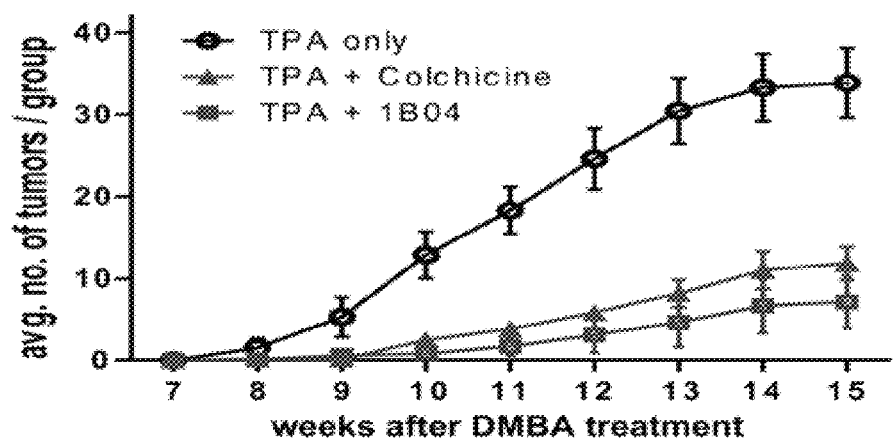
FIG. 11 is a diagram illustrating the average number of skin tumors and the volume thereof as well in the FVB/N mouse induced with skin tumor after treating the mouse with ethyl(2-methyl-3{(E)-[(naphtho[2,1-b]furan-2-ylcarbonyl)hydrazono]methyl}-1H-indole-1-yl)acetate and cholchicine.
A: average number of skin tumors; and
B: volume of skin tumor
Figure 11:
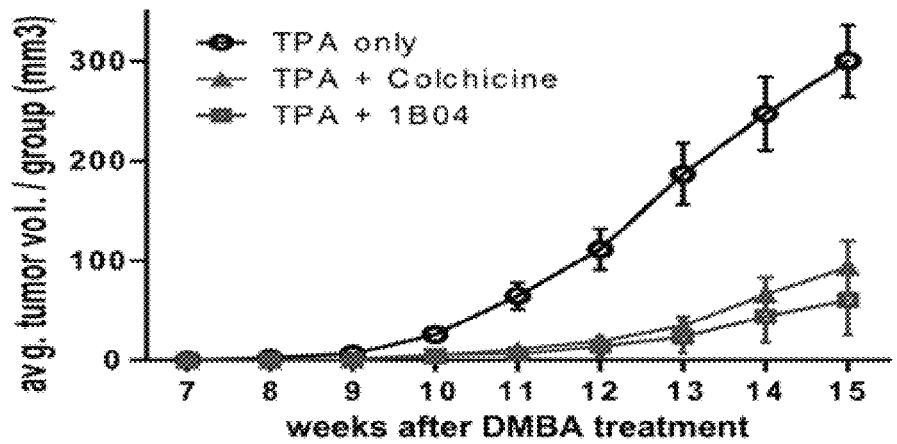

As a result, as shown in FIG. 11, the average number and the volume of skin tumor were significantly increased in the positive control treated with TPA. 15 weeks later when the experiment was terminated, the average number of skin tumor in the experimental group treated with cholchicine or ethyl(2-methyl-3{(E)-[(naphtho[2,1-b]furan-2-ylcarbonyl) hydrazono]methyl}-1H-indole-1-yl)acetate was 2.86 times or 4.75 times decreased, compared with that of the positive control. The average volume of skin tumor was 31.5% or 20.3% reduced, compared with that of the positive control.

Therefore, it was confirmed from the results of Example <8-3> that ethyl(2-methyl-3{(E)-[(naphtho[2,1-b]furan-2- ylcarbonyl)hydrazono]methyl}-1H-indole-1-yl)acetate and cholchicine displayed the significant anti-cancer activity in the mouse induced with skin tumor using DMBA/TPA.

<8-4> Confirmation of the Number of Mice Having Skin Tumor

Each mouse group was treated with different materials by the same manner as described in Example <8-2>, followed by observation for 15 weeks, and then the number of mice having skin tumor was counted. Tumor development rate was presented as %.

Figure 12:
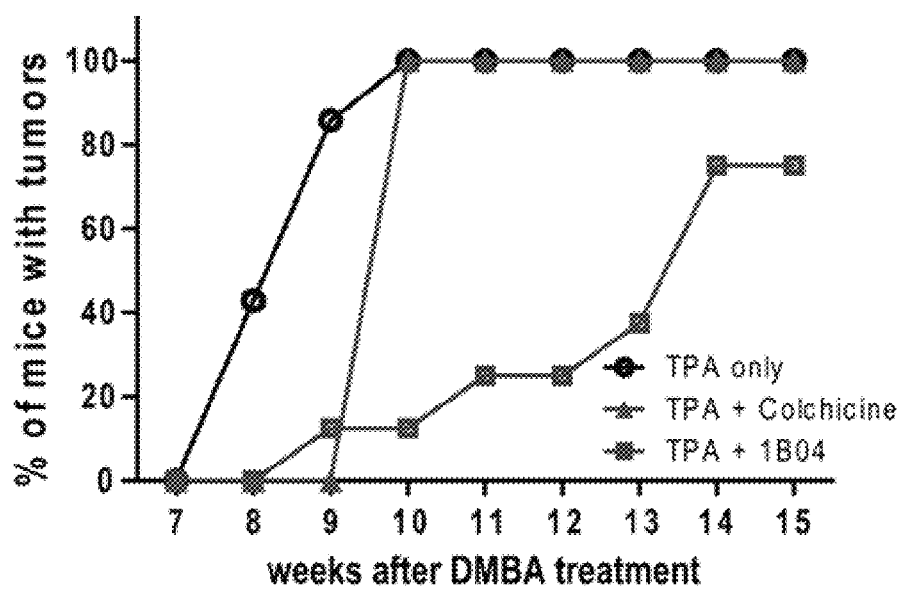
FIG. 12 is a diagram illustrating the number of the mouse confirmed to have skin tumor in the FVB/N mouse group induced with skin tumor.

As a result, as shown in FIG. 12, the tumor began to be formed from the 8$^{th}$ week (2 mm) in the positive control, and was grown 100% at the 10$^{th}$ week. In the meantime, the tumor formation in the experimental group treated with cholchicine or ethyl(2-methyl-3{(E)-[(naphtho[2,1-b]furan-2-ylcarbonyl)hydrazono]methyl}-1H-indole-1-yl)acetate was postponed to the 9$^{th}$ or the 10$^{th}$ week (FIG. 12).

<8-5> Investigation of the Average Weight of Tumor in the Mouse Induced with Skin Tumor by the Treatment of DMBA The mouse induced with skin tumor by the same manner as described in Example <8-2> was treated with DMBA, and then the induced tumors were observed and weighed for 15 weeks to produce the average weight of tumor.

Figure 13:
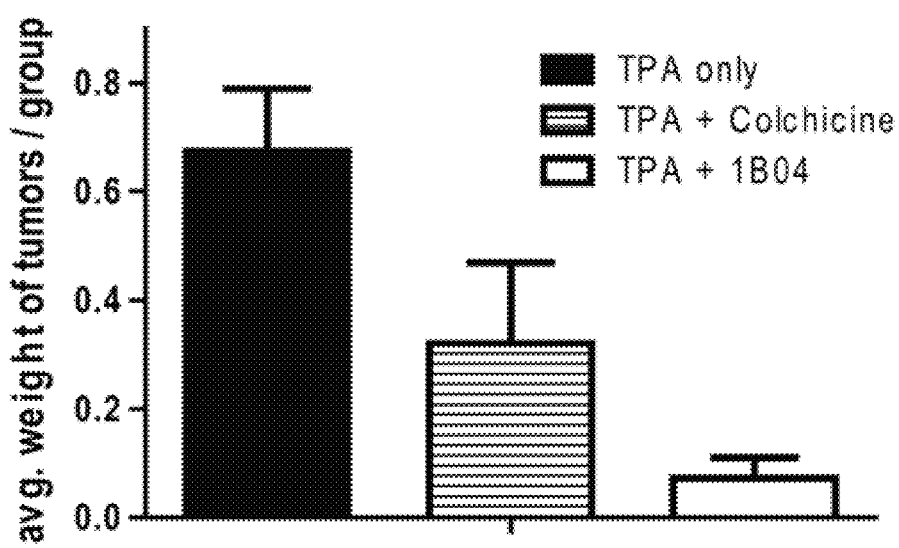
FIG. 13 is a diagram illustrating the average weight of tumor in the FVB/N mouse induced with skin tumor which was measured after inhibiting DMBA therein.

As a result, as shown in FIG. 13, the tumor of the experimental group treated with cholchicine or ethyl(2-methyl-3{(E)-[(naphtho[2,1-b]furan-2-ylcarbonyl)hydrazono]methyl}-1H-indole-1-yl)acetate was significantly lighter than that of the positive control. The average weight of the tumor of the experimental group 2 treated with ethyl(2-methyl-3{(E)-[(naphtho[2,1-b]furan-2-ylcarbonyl)hydrazono]methyl}-1H-indole-1-yl)acetate was only 1/10 by that of the tumor of the positive control (FIG. 13).

INDUSTRIAL APPLICABILITY

As described hereinbefore, ethyl(2-methyl-3{(E)-[(naphtho[2,1-b]furan-2-ylcarbonyl)hydrazono]methyl}-1H-indole-1-yl)acetate of the present invention or the pharmaceutically acceptable salts thereof can be effectively used for a pharmaceutical composition for the prevention or treatment of cell proliferative disease.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

We claim:

1. A method of treating cancer, comprising administering a pharmaceutically effective dose of a compound represented by the below formula 1 or a pharmaceutically acceptable salt thereof as an active ingredient to a subject having cancer:

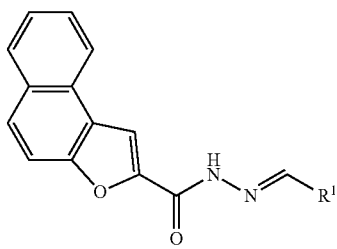

[Formula 1]

wherein
R$^1$ is

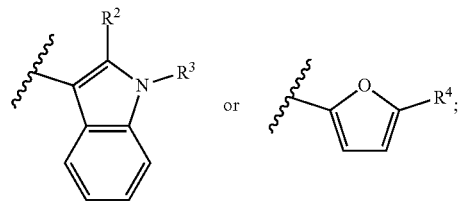

wherein R$^2$ is methyl, R$^3$ is methyl, allyl, cyanomethyl or —CH$_2$(C=O)OCH$_2$CH$_3$, and R$^4$ is nitro, 4-bromophenyl, 2,3-dichlorophenyl, 4-nitrophenyl or 4-methyl-3-nitrophenyl.

2. The method according to claim 1, wherein the compound represented by formula 1 is selected from the group consisting of the following compounds:
(1) ethyl(2-methyl-3{(E)-[(naphtho[2,1-b]furan-2-ylcarbonyl)hydrazono]methyl}-1H-indole-1-yl)acetate;
(2) (E)-N'-(1,2-dimethyl-1H-indol-3-yl)methylene) naphtho[2,1-b]furan-2-carbohydrazide;
(3) (E)-N'-((1-allyl-2-methyl-1H-indol-3-yl)methylene) naphtho[2,1-b]furan-2-carbohydrazide;
(4) (E)-N'''-((1-(cyanomethyl)-2-methyl-1H-indol-3-yl)methylene)naphtho[2,1-b]furan-2-carbohydrazide;
(5) (E)-N'-((5-(2,3-bromophenyl)furan-2-yl)methylene) naphtho[2,1-b]furan-2-carbohydrazide;
(6) (E)-N'-((5-2,3-dichlorophenyl)furan-2-yl)methylene) naphtho[2,1-b]furan-2-carbohydrazide
(7) (E)-N'-((5-(4-nitrophenyl)furan-2-yl)methylene)naphtho[2,1-b]furan-2-carbohydrazide;
(8) (E)-N'-((5-(4-methyl-3-nitrophenyl)furan-2-yl)methylene)naphtho[2,1-b]furan-2-carbohydrazide; and
(9) (E)-N'-((5-nitrofuran-2-yl)methylene)naphtho[2,1-b]furan-2-carbohydrazide.

3. The method according to claim 1, wherein the cancer is selected from the group consisting of rectal cancer, breast cancer, lung cancer, stomach cancer, liver cancer, leukemia, glioma, and uterine cervical cancer.

4. The method according to claim 1, wherein the compound represented by formula 1 induces microtubule depolymerization.

5. The method according to claim 1, wherein the compound represented by formula 1 characteristically binds to the cholchicine binding site of tubulin.

6. The method according to claim 1, wherein the compound represented by formula 1 induces apoptosis by arresting cell cycle in G2 or M phase.

7. The method according to claim 1, wherein the compound represented by formula 1 is effective against multi-drug-resistant cancer cells.

8. The method according to claim 1, wherein the cancer is selected from the group consisting of rectal cancer, lung cancer, stomach cancer, liver cancer, leukemia, and glioma.

\* \* \* \* \*